(12) United States Patent
Shimizu et al.

(10) Patent No.: US 9,006,483 B2
(45) Date of Patent: Apr. 14, 2015

(54) PROCESS FOR PRODUCING ACETIC ACID

(71) Applicant: Daicel Corporation, Osaka-shi, Osaka (JP)

(72) Inventors: Masahiko Shimizu, Tokyo (JP); Hiroyuki Miura, Himeji (JP); Takashi Ueno, Himeji (JP); Hidehiko Nakajima, Himeji (JP)

(73) Assignee: Daicel Corporation, Osaka-shi (JP)

( * ) Notice: Subject to any disclaimer, the term of this patent is extended or adjusted under 35 U.S.C. 154(b) by 0 days.

(21) Appl. No.: 14/378,049

(22) PCT Filed: Mar. 12, 2013

(86) PCT No.: PCT/JP2013/056766
§ 371 (c)(1),
(2) Date: Aug. 11, 2014

(87) PCT Pub. No.: WO2013/137236
PCT Pub. Date: Sep. 19, 2013

(65) Prior Publication Data
US 2015/0025270 A1 Jan. 22, 2015

(30) Foreign Application Priority Data

Mar. 14, 2012 (JP) ................................ 2012-057570

(51) Int. Cl.
*C07C 51/44* (2006.01)
*B01D 3/00* (2006.01)

(52) U.S. Cl.
CPC ................ *C07C 51/44* (2013.01); *B01D 3/009* (2013.01)

(58) Field of Classification Search
None
See application file for complete search history.

(56) References Cited

U.S. PATENT DOCUMENTS

| | | | |
|---|---|---|---|
| 3,791,935 A | 2/1974 | Eubanks et al. | |
| 4,039,395 A | 8/1977 | Eby | |
| 5,416,237 A | 5/1995 | Aubigne et al. | |
| 5,723,660 A | 3/1998 | Morimoto et al. | |
| 2008/0214866 A1 | 9/2008 | Miura et al. | |

FOREIGN PATENT DOCUMENTS

| | | |
|---|---|---|
| GB | 1350726 A | 4/1974 |
| JP | 48-56610 A | 8/1973 |
| JP | 52-23016 A | 2/1977 |
| JP | 6-40999 A | 2/1994 |
| JP | 2005-289936 A | 10/2005 |
| JP | 2006-160645 A | 6/2006 |
| JP | 2009-501129 A | 1/2009 |
| WO | WO 96/33965 A1 | 10/1996 |
| WO | WO 2007/007891 A2 | 1/2007 |

OTHER PUBLICATIONS

English translation of International Preliminary Report on Patentability and Written Opinion issued Sep. 25, 2014, in PCT International Application No. PCT/JP2013/056766.
International Search Report, issued in PCT/JP2013/056766, dated May 28, 2013.
English translation of the claims of Japanese Patent Laid-Open Publication No. 48-56610 (Aug. 9, 1973).

*Primary Examiner* — Yevegeny Valenrod
(74) *Attorney, Agent, or Firm* — Birch, Stewart, Kolasch & Birch, LLP

(57) ABSTRACT

A production process of acetic acid according to the present invention inhibits concentration of hydrogen iodide and improves a liquid-liquid separation of an overhead from a distillation column. Acetic acid is produced by distilling a mixture containing hydrogen iodide, water, acetic acid and methyl acetate in a first distillation column (3) to form an overhead and a side cut stream or bottom stream containing acetic acid, cooling and condensing the overhead in a condenser (C3) to form separated upper and lower phases in a decanter (4). According to this process, a zone having a high water concentration is formed in the distillation column above the feed position of the mixture by feeding a mixture having a water concentration of not less than an effective amount to not more than 5% by weight (e.g., 0.5 to 4.5% by weight) and a methyl acetate concentration of 0.5 to 9% by weight (e.g., 0.5 to 8% by weight) as the mixture to the distillation column and distilling the mixture. In the zone having a high water concentration, hydrogen iodide is allowed to react with methyl acetate to produce methyl iodide and acetic acid.

15 Claims, 2 Drawing Sheets

PROCESS FOR PRODUCING ACETIC ACID

TECHNICAL FIELD

The present invention relates to a process useful for producing high-quality acetic acid while inhibiting corrosion of an apparatus (e.g., a distillation column).

BACKGROUND ART

In regard to a process for producing acetic acid, an industrially used production process comprises allowing methanol to continuously react with carbon monoxide in the presence of a catalyst containing a group 8 metal of the Periodic Table (such as a rhodium catalyst or an iridium catalyst), an ionic iodide (e.g., lithium iodide), and methyl iodide and in the presence of water to give acetic acid. In this process, usually, a reaction mixture obtained by carbonylation of methanol is subjected to a flash distillation, the resulting volatile component from the flash distillation is distilled in a first distillation column to form an overhead from a top of the column and a heavy component from a bottom thereof, and an acetic acid stream is withdrawn as a side stream (side cut stream) from the first distillation column. Moreover, the overhead from the first distillation column is cooled and condensed to form an aqueous phase and an organic phase, which are separated from each other; the aqueous phase mainly contains water and acetaldehyde, and the organic phase mainly contains methyl iodide. Further, the acetic acid stream is subjected to a second distillation column to remove water and other impurities for obtaining or separating a further purified acetic acid stream as a side stream (side cut stream) or bottom stream. The second distillation column is mainly used for dehydration in many cases. Since an overhead from the top of the second distillation column has a low water content, the overhead is rarely separated into two phases (an aqueous phase and an organic phase) even after cooling and condensation. In such a process, accumulation of hydrogen iodide in the first and second distillation columns deteriorates the quality of product acetic acid due to contamination with hydrogen iodide and causes corrosion of an apparatus (such as the first and second distillation columns).

In order to remove hydrogen iodide, it has been reported that hydrogen iodide is converted into methyl iodide, having a lower boiling point, by a reaction of hydrogen iodide with methanol, and the resulting methyl iodide is separated as a lower boiling point stream.

Japanese Patent Application Laid-Open Publication No. 6-40999 (JP-6-40999A, Patent Document 1) discloses that introduction of a small quantity of methanol below a feed point, at which a feeding composition is fed to a distillation zone, converts hydrogen iodide into methyl iodide which is removed as a light end stream of a distillation column.

Japanese Patent Application Laid-Open Publication No. 52-23016 (JP-52-23016A, Patent Document 2) discloses a process for removing and collecting iodine-containing components and drying acetic acid, which comprises: introducing an acetic acid stream containing water, methyl iodide and hydrogen iodide into a first distillation zone intermediate; removing methyl iodide and others as an overhead fraction from the first distillation zone; removing hydrogen iodide and others from the bottom of the first distillation zone; withdrawing a side stream (acetic acid stream) from the middle section of the first distillation zone for introducing the stream into the upper section of a second distillation zone; introducing methanol into the lower section of the second distillation zone; removing an overhead stream containing methyl iodide and others from the second distillation zone; and withdrawing a stream of a product acetic acid substantially free of hydrogen iodide and methyl iodide from the bottom or a site near to the bottom of the second distillation zone.

Japanese Patent No. 4489487 (JP-4489487B, Patent Document 3) discloses a process for separating hydrogen iodide, which comprises distilling a mixture containing hydrogen iodide, water, and a component having a boiling point higher than that of water (e.g., acetic acid) to separate hydrogen iodide, wherein an alcohol (e.g., methanol) is fed to a distillation column so that a zone having a water concentration of 5% by weight in the distillation column may be formed between feed positions of the alcohol.

In the production of acetic acid, removal of hydrogen iodide by using the relationship between a water concentration and a hydrogen iodide concentration in a distillation column is also known. For example, Great Britain Patent No. 1350726 (Patent Document 4) discloses that because of a peak concentration of hydrogen halides occurring in a middle portion of a distillation column, if a side stream is withdrawn from the middle portion of the distillation column then the hydrogen halides will be removed therefrom, in a case where a liquid composition of carboxylic acid has a water concentration ranging from 3 to 8% by weight. Further, this document discloses that a reaction product of methanol and carbon monoxide is subjected to a flash distillation and then a fraction separated by the flash distillation is introduced into the distillation column to concentrate hydrogen iodide in a side stream from the middle portion of the distillation column, thereby removing the hydrogen iodide.

Japanese Patent Application Laid-Open Publication No. 2006-160645 (JP-2006-160645A, Patent Document 5) discloses a process for producing acetic acid, which comprises: distilling a mixture containing hydrogen iodide, water, methanol, methyl iodide, acetic acid and methyl acetate in a water content of not more than 5% by weight in a distillation column, withdrawing a fraction containing hydrogen iodide from the top of the column, and withdrawing acetic acid as a side-cut stream by side-cut or a stream from the bottom of the column to reduce the concentration of hydrogen iodide to not more than 50 ppm. According to this process, distillation at a water concentration of not more than 5% by weight in the distillation system allows inhibition of concentration of hydrogen iodide in the distillation system.

This document discloses that the mixture may be distilled by introducing at least one component selected from the group consisting of methanol, methyl acetate and an alkali metal hydroxide at an appropriate position of the distillation column (for example, at the bottom, or between the bottom and the middle section) for maintaining or keeping the water content of not more than 5% by weight in the distillation column and that such a process can remove hydrogen iodide. Further, Patent document 5 discloses in Examples and Comparative Examples that a liquid mixture containing 34% by weight of methyl iodide, 9.8% by weight of methyl acetate, 1.2% by weight of water, 55% by weight of acetic acid, and 190 ppm by weight of hydrogen iodide was distilled, and the resulting distillate from the top of the column was separated into an upper layer and a lower layer.

Although these processes can inhibit the concentration of hydrogen iodide in the distillation column, the hydrogen iodide removal efficiency is still insufficient to produce a high-quality acetic acid. Moreover, even if the overhead from the distillation column is condensed, the overhead is not efficiently separated sometimes into an aqueous phase (upper phase or light phase) and an organic phase (lower phase or heavy phase). In particular, when the liquid mixture is distilled and the overhead (fraction) from the column top is cooled and condensed according to Patent Document 5, the condensate has an inefficient separability into upper and lower phases. Further, even if the condensate is separated into the lower phase and the upper phase, it is impossible to stably perform or operate these processes due to an unsteady phase boundary (liquid interface) between these phases. Thus the continuous operation of the production apparatus sometimes confronts obstruction or trouble.

Japanese Patent Application Laid-Open Publication No. 2009-501129 (JP-2009-501129A, Patent Document 6) discloses a process for producing acetic acid, which comprises: separating a reaction mixture obtained by carbonylation of methanol into a catalyst stream and an acetic acid stream in a catalyst-separating column; in a first distillation column, separating the acetic acid stream into a first overhead containing methyl iodide, methyl acetate and a portion of water, and a first higher boiling point stream containing portions of water and propionic acid, and withdrawing a first side stream containing the acetic acid by side cut; feeding the first side stream to a second distillation column; and withdrawing and collecting a second side stream containing the acetic acid by side cut. This document discloses a process for reducing a concentration of a hydrogen halide contained in a product acetic acid, which comprises converting hydrogen iodide in the distillation column into methyl iodide and separating hydrogen iodide in the form of methyl iodide from the top of the distillation column to inhibit condensation of the hydrogen halide. The method for converting hydrogen iodide includes a method for feeding the first distillation column with water or water and a first component (A) (wherein the first component (A) is at least one member selected from the group consisting of methanol and methyl acetate) and a method for feeding the first distillation column with the first component (A) from a lower position relative to a first side stream port for side-cut of a first side stream. Moreover, the document states that because supply of water to the first distillation column develops (forms) a zone having a high water concentration in the distillation column and causes condensation of hydrogen halide in the zone, supply of water together with the first component (A) allows efficient conversion of hydrogen halide into a low-boiling component.

The patent document 6 discloses, in Examples, that methanol (4.9 mol/h), methyl acetate (7.4 mol/h) and water (21.1 mol/h) were fed from the 27th plate from the top of the distillation column (having 30 plates) (Examples 3 and 4), and methanol was fed from the 43th from the top of the distillation column (having 50 plates) (Comparative Example 2).

According to the process, unfortunately, a feeding liquid has a high concentration of methyl acetate, and in addition, the concentration of methyl acetate in an overhead fraction or stream (vapor phase component) from the top of the distillation column is further increased due to further condensation of methyl acetate in the distillation column and by-product methyl acetate formed by feeding of methanol. Thus, if the fraction from the top of the distillation column is cooled, the resulting condensate cannot be separated into an aqueous phase (an upper phase mainly containing water and acetaldehyde) and an organic phase (a lower phase mainly containing methyl iodide). Moreover, even if the condensate is separated into the phases, these phases are mixed to form a mixed phase due to a small difference in specific gravity between the light phase and the heavy phase, so that the distillation column cannot be operated stably. In particular, in an industrial process, the boundary (interface) between the aqueous phase and the organic phase varies depending on the rapid expansion of carbon monoxide in the reaction system, the flow rate and pressure fluctuations in the flash distillation step and others. Therefore, the aqueous phase and the organic phase cannot be separated clearly, so that the process apparatus cannot be operated continuously. Further, feeding of methanol or methyl acetate into the column from a position lower than a plate for feeding the mixture meaninglessly increases the diameter of the distillation column, resulting in low economic efficiency.

RELATED ART DOCUMENTS

Patent Documents

Patent Document 1: JP-6-40999A (Paragraph No. [0043])
Patent Document 2: JP-52-23016A (Claims, page 5, the lower right column, page 7, the lower left column to the lower right column)
Patent Document 3: JP-4489487B (Claims)
Patent Document 4: GB Patent No. 1350726 specification (page 2, lines 66 to 76)
Patent Document 5: JP-2006-160645A (Claims, Paragraph No. [0036])
Patent Document 6: JP-2009-501129A (Claims, Paragraph Nos. [0043] [0085], Examples 3 and 4, Comparative Example 2)

SUMMARY OF THE INVENTION

Problems to be Solved by the Invention

It is therefore an object of the present invention to provide a process for producing acetic acid, the process improving liquid-liquid separation of a low-boiling stream (overhead) from a distillation column while inhibiting condensation of hydrogen iodide, and a method for improving the liquid-liquid separation of the low-boiling stream (overhead).

Another object of the present invention is to provide a process for producing high-quality acetic acid by effectively inhibiting contamination with an impurity (e.g., hydrogen iodide), and a method for improving the quality of acetic acid.

It is still another object of the present invention to provide a process for producing acetic acid, useful for efficiently separating a low-boiling stream (overhead) into an aqueous phase and an organic phase by cooling and condensing the stream from a distillation column, and operating a production apparatus stably and continuously.

Means to Solve the Problems

The inventors of the present invention made intensive studies to achieve the above objects and finally found that distillation of a mixture under feeding of a decreasing agent (an agent for decreasing hydrogen iodide) to a distillation column achieves the followings (1) and (2), wherein the decreasing agent contains an effective amount of water in a concentration of not more than 5% by weight and an effective amount of methyl acetate in a concentration of not more than 9% by weight: (1) a zone having a high water concentration is formed in the distillation column above a charging site (feed site or part) of a volatile component to the distillation column, and methyl acetate is allowed to effectively react with hydrogen iodide in the high-concentration zone to produce methyl iodide (a lower boiling point component) and acetic acid, where methyl iodide has a high miscibility with an organic phase, contrarily acetic acid has a high miscibility with an aqueous phase and is largely different in boiling point from methyl iodide (largely different in boiling point from water formed by a reaction of methanol with hydrogen iodide); and (2) since a low-boiling stream (overhead) contains methyl acetate in a predetermined proportion, the low-boiling stream (overhead) from the distillation column is cooled and condensed to clearly and efficiently separate the resulting condensate into an organic phase containing methyl iodide and an aqueous phase containing acetic acid, and thus the liquid-liquid separation of the low-boiling stream (overhead) from the distillation column can significantly be improved. The present invention was accomplished based on the above findings.

That is, a process for producing acetic acid according to the present invention comprises: distilling a mixture containing hydrogen iodide, water, methyl iodide, acetic acid, and methyl acetate to form an overhead containing a lower boiling point component; and condensing the overhead to form separated liquid phases. In the process, acetic acid is produced by distilling a mixture containing an effective amount of water in a concentration of not more than 5% by weight and an effective amount of methyl acetate in a concentration of not more than 9% by weight (methyl acetate in a concentration of 0.5 to 9% by weight) to separate the mixture into an overhead (fraction) containing methyl iodide and a side cut stream or bottom stream containing acetic acid.

The mixture may has a methyl acetate concentration of 0.07 to 1.2 mol/L and a water concentration of 0.28 to 2.8 mol/L, and may be distilled continuously. The water content of the mixture may be about 0.5 to 4.5% by weight (e.g., about 1 to 4.3% by weight). The methyl acetate content of the mixture may be about 0.5 to 8% by weight (e.g., about 0.5 to 7.5% by weight or about 0.8 to 7.5% by weight). The mixture may further contain dimethyl ether. The concentration of dimethyl ether may be about 0.15 to 3% by weight.

The mixture may be fed to a distillation column from an intermediate or lower position of the distillation column in height. Moreover, a zone having a high water concentration may be formed inside a distillation column at a position upper than a feed position at which the mixture is fed to the distillation column; in the high water concentration zone, hydrogen iodide may be allowed to react with methyl acetate to produce methyl iodide and acetic acid; and the distillation may provide the overhead containing the resulting methyl iodide.

The present invention includes the process for producing acetic acid, in which methanol is allowed to continuously react with carbon monoxide by using a catalyst containing a group 8 metal of the Periodic Table (such as a rhodium catalyst or an iridium catalyst), an ionic iodide (e.g., lithium iodide), and methyl iodide in the presence of water; the reaction product is separated into a low-volatile phase component and a volatile phase component by a flash distillation; the volatile phase component as the mixture is distilled to form the overhead containing methyl iodide and the side cut stream or bottom stream (or the side cut stream and the bottom stream) containing acetic acid; and the overhead is condensed to form an aqueous phase and an organic phase. In the process for producing acetic acid, the volatile phase component is distilled while being adjusted to a water concentration of an effective amount and not more than 5% by weight and a methyl acetate concentration of 0.5 to 9% by weight in a distillation atmosphere of the volatile phase component in terms of a condensate or liquid form.

At least one member selected from the group consisting of methyl acetate, methanol and dimethyl ether, and if necessary water, may be added (or supplied) to the mixture (volatile phase component) or a distillation atmosphere of the mixture (volatile phase component) to adjust the concentrations of water and methyl acetate, and the resulting volatile phase component may be distilled. Moreover, a distillation atmosphere of a volatile phase component may be formed in the distillation column at a height equal to or upper than a feed site of the volatile phase component.

Further, the mixture may have a hydrogen iodide concentration of about 100 to 10000 ppm. Such a mixture may be subjected to a distillation to form (or separate) a side cut stream containing acetic acid. The concentration of hydrogen iodide in the side cut stream may be about 1 to 350 ppm.

Furthermore, in order to efficiently separate the overhead into an aqueous phase and an organic phase by condensation of the overhead, the separated lower phase (organic phase or heavy phase) may have a methyl acetate concentration of about 1 to 15% by weight, and the upper phase (aqueous phase or light phase) may have a lower methyl acetate concentration of about 0.4 to 8% by weight than the lower phase has.

The present invention also includes a method for liquid-liquid separating a condensate, comprising: distilling a mixture containing hydrogen iodide, water, methyl iodide, acetic acid, and methyl acetate to form an overhead containing a lower boiling point component, and condensing the overhead. In this method, the mixture containing an effective amount of water in a concentration of not more than 5% by weight and methyl acetate in a concentration of 0.5 to 9% by weight is distilled to reduce a concentration of hydrogen iodide in the overhead and a side cut stream, and the condensation of the overhead improves the liquid-liquid separation of the condensate. In the method, the concentration of hydrogen iodide in the overhead and the side cut stream may be reduced by adjusting a concentration of methyl acetate in the mixture to 0.5 to 8% by weight (or by increasing a concentration of methyl acetate in the mixture within the range of 0.4 to 8% by weight). Further, the liquid-liquid separation of the condensate may be improved by adjusting (or controlling) concentrations of methyl iodide and methyl acetate in the lower phase (organic phase or heavy phase) to 76 to 98% by weight and 1 to 15% by weight, respectively (with the proviso that the total of components in the lower phase (organic phase or heavy phase) is 100% by weight), and adjusting (or controlling) concentrations of water and methyl acetate in the upper phase (aqueous phase or light phase) are adjusted to 50 to 90% by weight and 0.4 to 8% by weight, respectively (with the proviso that the total of components in the upper phase (aqueous phase or light phase) is 100% by weight).

The present invention also includes an apparatus for producing acetic acid by distilling a mixture containing hydrogen iodide, water, methyl iodide, acetic acid, and methyl acetate. The apparatus comprises a controller for adjusting (or setting to or controlling) a water concentration in the mixture to not less than an effective amount to not more than 5% by weight and a methyl acetate concentration therein to 0.5 to 9% by weight by feeding water and/or methyl acetate, and further comprises a distillation column for distilling the mixture having adjusted water concentration and methyl acetate concentration to form (or provide) an overhead containing methyl iodide and a side cut stream or bottom stream containing acetic acid, a cooling unit (a condenser) for cooling the overhead from the distillation column, and a liquid-liquid-separating unit (a decanter) for separating the resulting condensate of the cooled overhead into two phases.

As used herein, the term "mixture" is sometimes the same meaning as a volatile phase component obtained by flash distillation. Moreover, an amount of a component in the mixture means not an amount of the component in a vapor phase but an amount of the component in the form of the condensate or liquid.

Effects of the Invention

According to the present invention, since a mixture containing a specific concentration of water and a specific concentration of methyl acetate is distilled to form separated phases, the concentration of hydrogen iodide (or corrosion of an apparatus) can be inhibited and the liquid-liquid separation of a low-boiling stream (overhead) from a distillation column can be improved. Moreover, due to the conversion of hydrogen iodide into methyl iodide and the separation of the overhead into an aqueous phase and an organic phase, the present invention effectively prevents contamination with an impurity (such as hydrogen iodide) to produce high-quality acetic acid. Further, cooling and condensing the low-boiling stream (overhead) from the distillation column allows efficient separation of the stream into the aqueous phase and the organic phase, so that a production apparatus can be stably and continuously operated. Thus, the present invention is useful as a process for industrially producing acetic acid.

DESCRIPTION OF EMBODIMENTS

Figure 1:
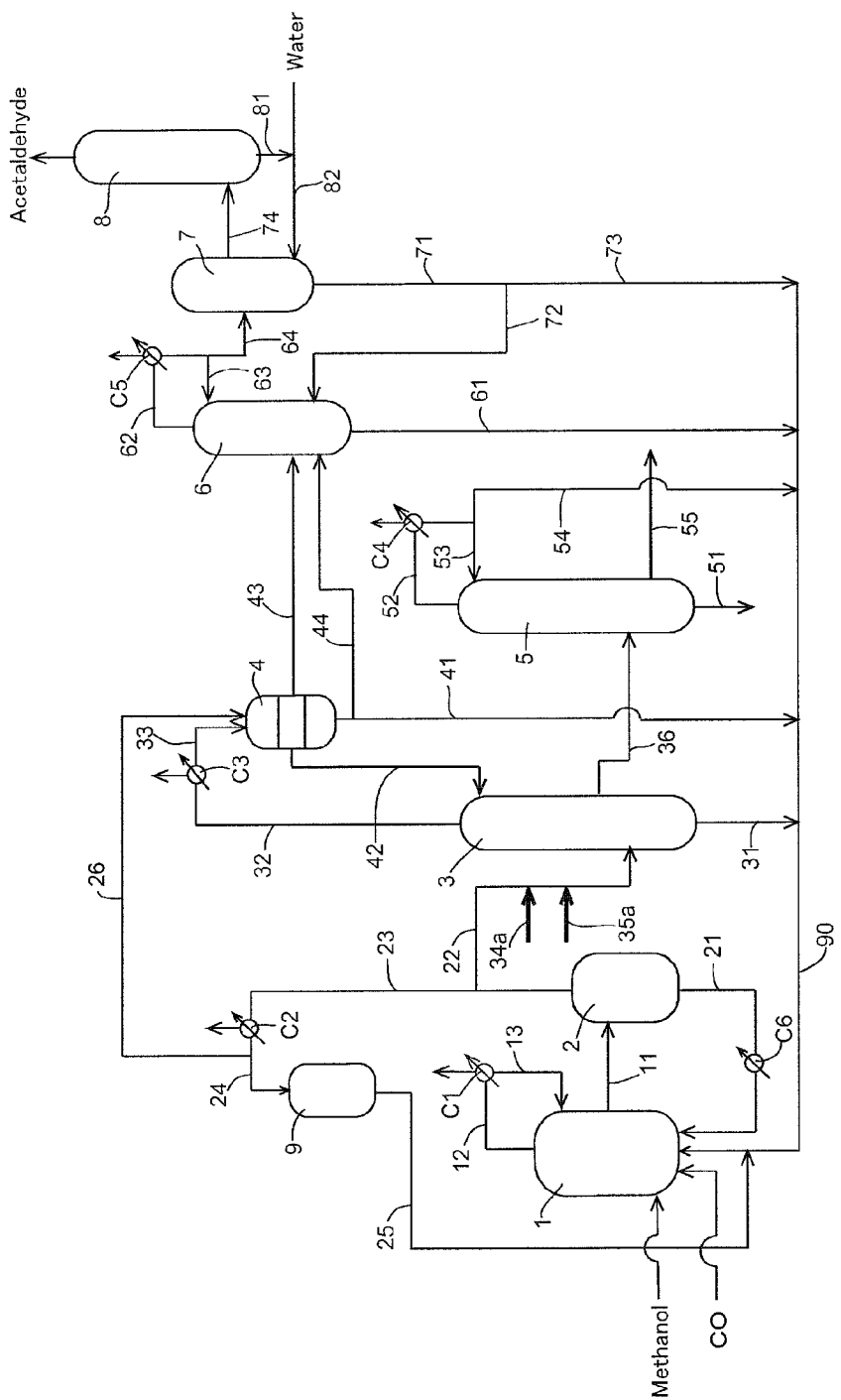
FIG. 1 is a diagram for explaining a production process of acetic acid in accordance with an embodiment of the present invention.

Hereinafter, the present invention will be explained in detail with reference to the drawings if necessary. FIG. 1 is a diagram (a flow sheet, a schematic process drawing, or a schematic plant layout drawing) for explaining a production process (or production apparatus) of acetic acid in accordance with an embodiment of the present invention.

The process (or production apparatus) shown in FIG. 1 comprises a reactor (reaction system) 1 for allowing methanol to continuously react with carbon monoxide (carrying out the carbonylation reaction of methanol) in the presence of a catalyst (or a catalyst system and water; a flasher or evaporator (flash evaporator) 2 for separating the reaction mixture (liquid reaction medium) into a volatile phase component and a low-volatile phase component; a first distillation column (splitter column) 3 for distilling the volatile phase component to form (or provide) a first overhead from a top of the column, a bottom stream from a bottom thereof, and a side cut stream (crude acetic acid stream); a decanter 4 for cooling and condensing the first overhead in a condenser C3 and for separating the first overhead into an aqueous phase (upper phase or light phase) and an organic phase (lower phase or heavy phase); a second distillation column (dehydration column or purification column) 5 for distilling the side cut stream (crude acetic acid stream) from the first distillation column 3 to form a second overhead from a top of the second distillation column, a bottom stream from a bottom thereof, and a side cut stream (purified acetic acid stream) from a side thereof; and an impurity-removing system [a third distillation column 6, a water extraction column (water extractor) 7, and a fourth distillation column 8] for removing an impurity from a condensate (an aqueous phase and an organic phase) in a condenser C4.

Methanol (a liquid reactant) and carbon monoxide (a gaseous reactant) are continuously fed to the reactor 1 at predetermined rates in the presence of a catalyst system (carbonylation catalyst system) containing a metal catalyst (such as a rhodium catalyst or an iridium catalyst) and a co-catalyst [lithium iodide as an ionic iodide (or iodide salt) and methyl iodide] and a definite amount of water, and the carbonylation reaction of methanol is continuously conducted. The reaction system usually contains acetic acid, which is a reaction product and also functions as a reaction solvent, and methyl acetate, which is by-produced from a reaction of acetic acid with methanol. Inside the reactor 1, a liquid-phase reaction system containing the metal catalyst component (such as a rhodium catalyst), the ionic iodide (such as lithium iodide), methanol, acetic acid, and others is in equilibrium with a vapor-phase system containing unreacted carbon monoxide and gaseous by-products derived from the reaction (hydrogen, methane, carbon dioxide), a vaporized low-boiling component (e.g., methyl iodide, acetic acid as a product, methyl acetate, acetaldehyde, and hydrogen iodide), and others.

In order to keep the inner pressure of the reactor 1 (e.g., reaction pressure, carbon monoxide partial pressure, and hydrogen partial pressure) constant, a vapor stream is withdrawn from the top through a discharge line 12 and cooled in a condenser C1. A condensed liquid component (containing acetic acid, methyl acetate, methyl iodide, acetaldehyde, water, and others) in the condenser is recycled (or refluxed) to the reactor 1 through a recycle line (or reflux line) 13, and an uncondensed gaseous component (containing carbon monoxide, hydrogen, and others) in the condenser is discharged as offgas. In particular, the reaction system is an exothermic reaction system accompanying heat generation, and part of the quantity of heat generated in the reactor 1 is removed by cooling the vapor component from the reactor 1 in the condenser C1 and recycling the condensed component to the reactor 1.

Components contained in the reaction mixture (crude reaction liquid) may include acetic acid, a volatile component having a boiling point lower than that of acetic acid [e.g., a low-boiling component (e.g., methyl iodide as a co-catalyst, methyl acetate as a reaction product of acetic acid with methanol, methanol, water, and dimethyl ether) or a low-boiling impurity (hydrogen iodide, acetaldehyde, crotonaldehyde)], and a low-volatile component having a boiling point higher than that of acetic acid [e.g., a metal catalyst component (a rhodium catalyst, and lithium iodide as a co-catalyst) or a high-boiling impurity (for example, a by-product, e.g., propionic acid, an aldehyde condensation product such as 2-ethylcrotonaldehyde, and a $C_{6-12}$alkyl iodide such as hexyl iodide or decyl iodide)].

Accordingly, the reaction mixture (a portion of the reaction mixture) is continuously fed from the reactor 1 to the flasher or evaporator (flash evaporator, flash distillation column) 2 through a feed line 11 for a flash distillation, and separated into a volatile phase component from the column top or upper part (or section) of the flash evaporator 2 (a lower boiling point fraction mainly containing acetic acid as a product, methanol, methyl acetate, methyl iodide, water, propionic acid, acetaldehyde, and hydrogen iodide as a by-product) and a low-volatile phase component (a higher boiling point fraction mainly containing a metal catalyst component (high-boiling component) such as a rhodium catalyst and a lithium iodide).

The low-volatile phase component (liquid catalyst mixture or bottom fraction) may be recycled to the reactor 1 through a recycle line 21. In this embodiment, the low-volatile phase component (liquid catalyst mixture or bottom fraction) is continuously withdrawn through a recycle line 21 from the bottom of the evaporator 2 and heat-removed and cooled in a heat exchanger (a condenser C6), and the cooled low-volatile phase component (liquid catalyst mixture) is recycled to the reactor 1. Thus, the temperature of the reactor 1 is easily controlled. The low-volatile phase component (liquid catalyst mixture) usually contains the metal catalyst component, and in addition, components remaining without evaporation (e.g., acetic acid, methyl iodide, water, and methyl acetate).

A portion of the volatile phase component (or volatile phase) from the evaporator 2 is introduced into a condenser (heat exchanger) C2 through a feed line 23, and cooled and separated into a condensed component containing acetic acid (a liquid component containing acetic acid, methanol, methyl acetate, methyl iodide, water, propionic acid, acetaldehyde, hydrogen iodide, and others) and a noncondensed component (a gas component such as carbon monoxide or hydrogen). A portion of the condensed component (liquid component) is retained in a buffer tank 9 and recycled to the reactor 1 through a recycle line 25, the other portion (remainder) of the condensed component (liquid component) is fed to the decanter 4 through a line 26, and the noncondensed component (gas component) is discharged as a vent gas. In this manner, since a portion of the volatile phase component from the flash evaporator 2 is cooled and efficiently heat-removed in the condenser (heat exchanger) C2 and then recycled to the reactor 1, the temperature of the reactor 1 is easily controlled. Accordingly, since the succeeding distillation column(s) or condenser(s) can be downsized (or miniaturized) even for a large-sized plant, acetic acid can be produced with a high purity in a resource-saving and energy-saving equipment. In particular, according to the process shown in FIG. 1, the low-volatile phase component (liquid catalyst mixture or bottom fraction) and a portion of the volatile phase component (or volatile phase) are cooled and recycled to the reactor 1. Thus even when the reactor is not necessarily equipped with a heat-removable (or heat-removing) or cooling unit (e.g., an external circulation cooling unit such as a jacket), the heat removal can be achieved.

The volatile phase component (or volatile phase) is fed to a lower-middle part, in a height direction, of the first distillation column (splitter column) 3 (e.g., a plate column) through a feed line 22. That is, a portion of the volatile phase component (or volatile phase) fed through the feed line 22 is distilled in the first distillation column (splitter column) 3 and separated into a first overhead (a first lower boiling point component containing methyl iodide, methyl acetate, acetaldehyde, water, and others) withdrawn from the column top or upper part (or site) of the column, a bottom stream [a stream mainly containing a higher boiling point component, e.g., a high-boiling impurity such as water, acetic acid, an entrained catalyst (such as lithium iodide), propionic acid, a $C_{6-12}$alkyl iodide (such as hexyl iodide), or an aldehyde condensation product] withdrawn from the column bottom, and a side cut stream [a first liquid stream (crude acetic acid stream) mainly containing acetic acid] from the side (a site upper than the feed site (or feed section) of the feed line 22). In this embodiment, the side cut stream (crude acetic acid stream) is fed to the second distillation column 5 through a feed line 36, and the bottom stream from the column bottom is fed to the reactor 1 through a recycle line 31. A portion or all of the bottom stream from the column bottom may be recycled to the evaporator 2 through a line (not shown).

The first overhead is introduced into the condenser C3 through an introduction line 32 and cooled and condensed. The resulting condensed component (a condensate containing methyl iodide, methyl acetate, acetic acid, acetaldehyde, and others) is fed to the decanter 4 through an introduction line 33, and the resulting noncondensed component (a gas component mainly containing carbon monoxide, hydrogen, and others) is discharged as a vent gas.

In order to inhibit the corrosion of the distillation column 3 and improve the liquid-liquid separation of the condensate in the decanter 4, the volatile component fed to the distillation column 3 through the feed line 22 contains not more than 5% by weight (e.g., 1 to 3% by weight) of water and 0.5 to 9% by weight (e.g., 3 to 5% by weight) of methyl acetate, in terms of condensate or liquid. In this embodiment, a water supply line 34a and a methyl acetate supply line 35a are connected to the feed line 22 for adjusting (or controlling) the water concentration of and methyl acetate concentration in the distillation column 3 (the concentrations in the volatile component).

More specifically, due to a low water concentration in the volatile component, a zone having a high water concentration appears above the feed site of the volatile component in the first distillation column 3. In this zone, although highly water-soluble hydrogen iodide is concentrated, feeding of methyl acetate predominantly proceeds with a reaction of methyl acetate with hydrogen iodide to shift the following equilibrium reaction (1) rightward. Thus useful methyl iodide and acetic acid can be obtained. Further, feeding of water and/or methyl acetate can shift the following equilibrium reaction (2) rightward to form methanol and acetic acid. The following reaction (3) of the resulting methanol with hydrogen iodide can produce useful methyl iodide and water. That is, finally, while production of hydrogen iodide as a by-product (shift reaction of the equilibrium reaction (3) leftward) is inhibited, methyl iodide (which has a high affinity with an organic phase and a low boiling point), acetic acid (which has a high affinity with water and has a high boiling point) and water are produced. Thus, methyl iodide, acetic acid and water can be separated effectively by distillation. In addition, as described below, in the decanter 4 these components can be separated efficiently into an organic phase mainly containing methyl iodide and an aqueous phase mainly containing water and acetic acid.

$$CH_3COOCH_3 + HI \leftrightarrow CH_3I + CH_3COOH \quad (1)$$

$$CH_3COOCH_3 + H_2O \leftrightarrow CH_3OH + CH_3COOH \quad (2)$$

$$CH_3OH + HI \leftrightarrow CH_3I + H_2O \quad (3)$$

Further, usually, since a reflux site of the condensate (liquid reflux mixture) in the first distillation column 3 is located in an upper part (or site) of the first distillation column 3 and a distribution of the water concentration (distribution of the water concentration containing a water concentration of about 5%) is formed inside the first distillation column 3, the feed site of the condensate (liquid reflux mixture) fed from the decanter 4 to the first distillation column 3 through a reflux line 42 is located or positioned above a zone having a high water concentration and a high hydrogen iodide concentration. Specifically, the zone having high water and hydrogen iodide concentrations is formed between the feed site of the volatile component and the feed site of the liquid reflux mixture. Moreover, when the water concentration is less than 5% by weight in the head of the distillation column 3, a zone having a high hydrogen iodide concentration is not formed in the column 3. Thus, water or methyl iodide in the condensate (liquid reflux mixture) can effectively disturb the production of hydrogen iodide as a by-product in the zone having high water and hydrogen iodide concentrations.

Furthermore, even if the low-boiling stream (overhead) from the distillation column 3 is contaminated with unreacted hydrogen iodide, having a low boiling point, the unreacted hydrogen iodide can be condensed in an aqueous phase in the decanter 4 by condensing the low-boiling stream (overhead) in the condenser C3, so that the crude acetic acid stream as a side cut stream can be prevented from contamination with hydrogen iodide.

The feed amounts (supplies) of water and/or methyl acetate through the water supply line 34a and the methyl acetate supply line 35a can be calculated based on an analysis of the condensate condensed in the condenser C2 or the volatile phase component (or volatile phase) in the line 22 or 23, in particular, the water and methyl acetate concentration, and a flow rate of the volatile phase component (or volatile phase). The calculated feed amount (flow rate) of water and that of methyl acetate are fed to the line 34a and the line 35a, respectively, and thus the water and methyl acetate concentrations in the column can be adjusted to predetermined concentrations.

A portion of the condensate condensed in the condenser C3 is recycled to the reactor 1 through a recycle line 41, and another portion of the condensate is recycled to the first distillation column 3 through a reflux line 42 for reflux. More specifically, in the decanter 4, the condensate of the first overhead cooled and condensed in the condenser C3 is separated into an aqueous phase (upper phase or light phase) and an organic phase (lower phase or heavy phase); wherein the aqueous phase contains water, acetic acid, methyl acetate, hydrogen iodide, acetaldehyde, and others, and the organic phase contains methyl iodide, methyl acetate, and others. The aqueous phase (upper phase) is fed to the first distillation column 3 through the reflux line 42 for reflux. The organic phase (lower phase) is recycled to the reactor 1 through the recycle line 41.

The methyl acetate concentration is greatly involved in or engaged with the liquid-liquid separation of the condensate. In other words, since methyl acetate is miscible with both aqueous phase and organic phase, a high concentration of methyl acetate sometimes produces the uniform (or homogenous) condensate without liquid-liquid separation. The formation of the uniform or homogenous condensate fails to reuse useful methyl iodide as a catalyst system, and requires a further purification means in order to separate and collect acetic acid. In contrast, according to the present invention, as described above, since the volatile phase component (distillation system) containing a predetermined concentration of water and that of methyl acetate is distilled in the first distillation column 3 and the overhead is condensed, the aqueous phase and the organic phase can be separated clearly. Thus the present invention advantageously allows collection or reuse of a useful component and separation and removal of an impurity component.

The side cut stream (crude acetic acid stream) from the first distillation column 3 is fed to the second distillation column (dehydration column or purification column) 5 through the feed line 36 and distilled for separating into or providing a second overhead (a second lower boiling point component containing a low-boiling component such as water) withdrawn from the column top through a line 52, a bottom stream [a high-boiling component (a high-boiling impurity) containing water, a carboxylic acid having a high boiling point (such as propionic acid), a $C_{6-12}$alkyl iodide (such as hexyl iodide), an aldehyde condensation product, and others] withdrawn from the column bottom through a line 51, and a side cut stream [a second liquid stream containing acetic acid (purified acetic acid stream with a high purity)] withdrawn from the side (between the column bottom and the feed site of the feed line 36) through a line 55.

The second overhead (lower boiling point fraction) is sent to the condenser C4 through a discharge line 52 and cooled and condensed. A portion of the condensate (the condensate mainly containing water) is fed to the second distillation column 5 through a reflux line 53 for reflux, and another portion thereof is recycled to the reactor 1 through a recycle line 54. The uncondensed gaseous component (gas) is discharged as an offgas.

Further, in the process shown in FIG. 1, an impurity (e.g., hydrogen iodide and acetaldehyde) is separated and removed. Specifically, the condensate (a portion of the aqueous phase and organic phase) condensed in the decanter 4 is fed to the third distillation column 6 through a line 43 and/or a line 44 and separated into a third overhead (a low-boiling stream containing hydrogen iodide, acetaldehyde, methyl iodide, water, and others) from the column top and a bottom stream (a high-boiling stream containing water, acetic acid, and others) from the column bottom. The third overhead is fed to a condenser C5 through a discharge line 62 and cooled and condensed. The resulting condensate mainly containing acetaldehyde is returned to the third distillation column 6 through a reflux line 63 for reflux. The resulting noncondensed component (gas component) is discharged as an offgas. Moreover, the bottom fraction is recycled to the reactor through recycle lines 61, 90.

Further, the condensate in the condenser C5 is fed to an extractor 7 through a line 64. In the extractor, a water-soluble component (e.g., acetaldehyde) is extracted with water fed through a water feed line 82, and thus the condensate is separated into a water-extracted phase (an aqueous phase or upper phase mainly containing acetaldehyde) and an organic phase (a lower phase or raffinate mainly containing methyl iodide). The extracted phase (aqueous phase) is fed to a fourth distillation column 8 through a line 74 and separated into a low-boiling stream (a fraction mainly containing acetaldehyde and others) from the column top and a bottom stream (a fraction mainly containing water) from the column bottom. Moreover, a portion of the organic phase (raffinate) in the extractor 7 is fed to the third distillation column 6 through lines 71, 72, and another portion thereof is recycled to the reactor 1 through recycle lines 73, 90. The bottom stream from the fourth distillation column 8 is joined to (or combined to) water of the water feed line 82 through a line 81, and used for water extraction in the extractor 7. The low-boiling stream (a fraction mainly containing acetaldehyde) from the column top of the fourth distillation column 8 is discharged as an offgas.

According to the process (or production apparatus), the water concentration and the methyl acetate concentration in the distillation system of the first distillation column 3 are adjusted to not more than 5% by weight (for example, 1 to 3% by weight) and 0.5 to 9% by weight (for example, 3 to 5% by weight), respectively, by feeding water and/or methyl acetate through the water feed line 34a and the methyl acetate feed line 35a. Thus, the zone having a high hydrogen iodide concentration can be formed in a predetermined zone in the first distillation column 3; and hydrogen iodide is allowed to contact with an ascending stream of methyl acetate (and methanol) having a low boiling point in the volatile phase component, so that the reaction can convert hydrogen iodide into methyl iodide to produce acetic acid and water as by-products. Further, in the decanter 4, since the methyl acetate content can be reduced, the aqueous phase (mainly containing acetic acid, methyl acetate and hydrogen iodide) and an organic phase (mainly containing methyl iodide and methyl acetate) can be separated with a high liquid-liquid separation efficiency. Thus, the side cut stream (crude acetic acid stream) from the first distillation column 3 can be prevented from contamination with hydrogen iodide, a load on the second distillation column 5 can be decreased and the corrosion of the first and second distillation columns 3, 5 can be inhibited.

Figure 2:
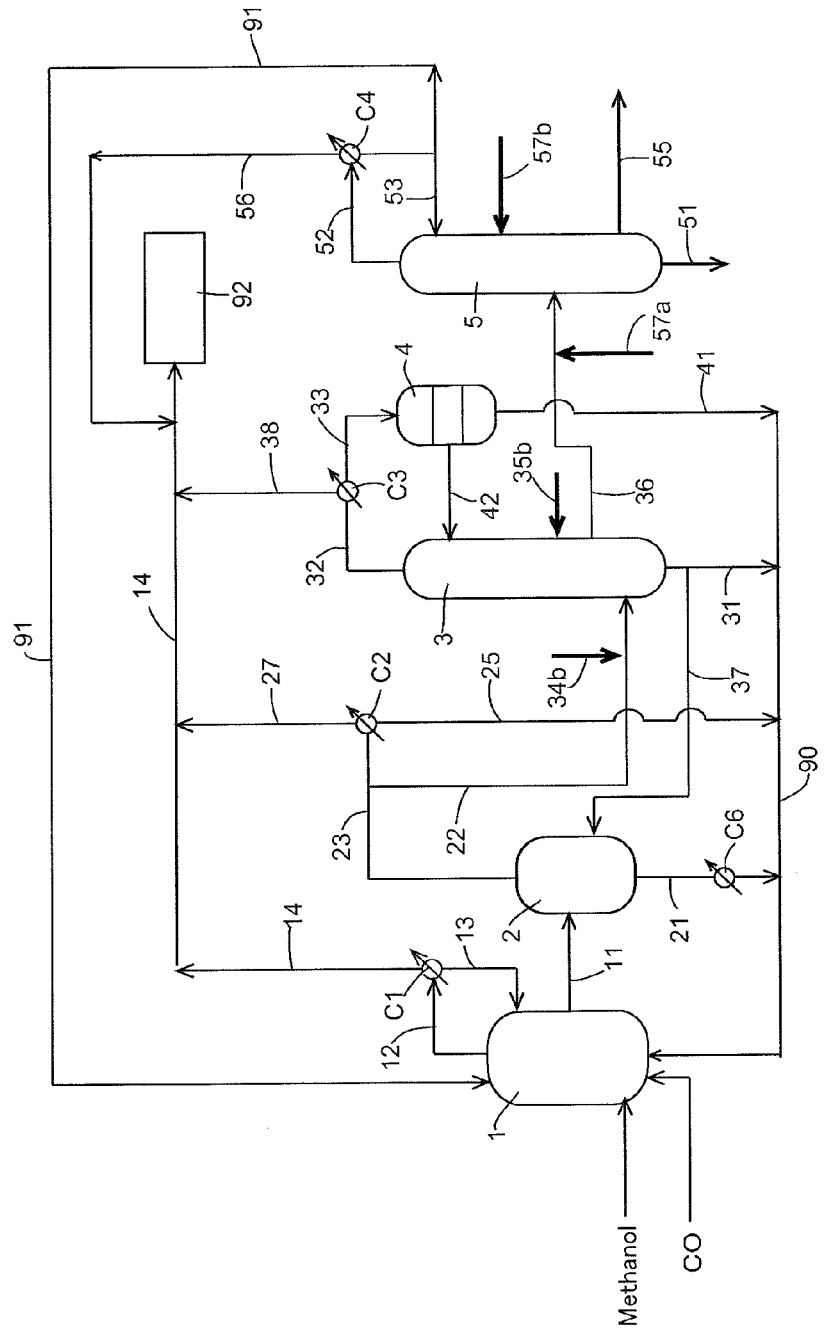
FIG. 2 is a diagram for explaining a production process of acetic acid in accordance with another embodiment of the present invention.

FIG. 2 is a flow diagram for explaining a process (or apparatus) producing for acetic acid in accordance with another embodiment of the present invention. For explanation, the same reference numeral as that in FIG. 1 is given to the substantially same element as that in FIG. 1.

In this embodiment, acetic acid is produced by basically the same process as that shown in FIG. 1 except that (i) a condensate obtained by condensing a volatile phase component from a flash evaporator 2 is not fed to a decanter 4, (ii) separation processes (a third distillation column, a water extractor, a fourth distillation column) for further separating or removing an impurity from the condensate in the decanter 4 are not shown, (iii) an offgas from each condenser C1 to C4 is treated by a scrubber system, and (iv) in a second distillation column 5, hydrogen iodide is further removed by addition of an alkali component.

More specifically, a vapor phase is withdrawn from a reactor 1 through a discharge line 12 and cooled in a condenser C1; the resulting condensed liquid component is returned to the reactor 1 through a reflux line 13 for reflux, and the resulting noncondensed component (gaseous component) is sent to a scrubber system 92 through a discharge line 14. Moreover, a reaction mixture in the reactor 1 is fed to a flash evaporator 2 through a feed line 11 and subjected to a flash distillation; a portion of the resulting volatile phase component is fed to a first distillation column 3 through a feed line 22, and another portion of the volatile phase component passes through a feed line 23 and cooled and condensed in a condenser C2 to produce a condensate and a noncondensed component. The condensate is recycled to the reactor 1 through a recycle line 25, and the noncondensed component (gaseous component) is fed to the scrubber system 92 through a discharge line 27. In this embodiment, the position (feed port) of a feed line 22 connected to the first distillation column 3 is located between the bottom and the intermediate of the first distillation column 3.

Moreover, in the first distillation column 3, the volatile phase component from the flash evaporator 2 is distilled to give a first overhead withdrawn from the column top, a bottom stream withdrawn from the column bottom, and a side cut stream (crude acetic acid stream) from the side. The side cut stream is withdrawn from a site above the position (feed port) of the feed line 22 connected to the first distillation column 3. The first overhead is introduced into a condenser C3 through an introduction line 32 and is cooled and condensed to give a condensed component and a noncondensed component; the condensed component (a condensate containing methyl, iodide, methyl acetate, acetic acid, acetaldehyde, and others) is fed to a decanter 4 through an introduction line 33, and the noncondensed component (a gas component mainly containing carbon monoxide, hydrogen, and others) is fed to the scrubber system 92 through a discharge line 38. A portion of the bottom stream is returned to a flash evaporator 2 through a line 37, and another portion of the bottom stream is recycled to the reactor 1 through a recycle line 31. All of the bottom stream may be returned to the flash evaporator 2 through the line 37. A condensate in the decanter 4 (in this embodiment, an aqueous phase) is returned to the first distillation column 3 through a reflux line 42 for reflux. A condensate in the decanter 4 (in this embodiment, an organic phase) is recycled to the reactor 1 through a recycle line 41.

Further, the side cut stream from the first distillation column 3 is fed to a second distillation column (dehydration column or purification column) 5 through a feed line 36 and is separated, by distillation in the second distillation column 5, into a second overhead withdrawn from the column top through a line 52, a bottom stream withdrawn from the column bottom through a line 51, and a side cut stream (high-purity acetic acid stream) withdrawn from the side through a line 55. The second overhead (lower boiling point fraction) passes through a discharge line 52 and is cooled and condensed in a condenser C4 to give a condensate and a noncondensed component. A portion of the condensate (a condensate mainly containing water) is returned to the second distillation column 5 through a reflux line 53 for reflux, and another portion of the condensate is recycled to the reactor 1 through a recycle line 91. Moreover, the noncondensed component (gaseous component) is fed to the scrubber system 92 through a discharge line 56.

In the scrubber system 92, a useful component (e.g., methyl iodide, acetic acid) is collected and recycled to the reactor 1, and carbon monoxide is purified by PSA (pressure swing adsorption) or other methods and recycled to the reactor 1.

To the feed line 22 for feeding the volatile phase component to the first distillation column 3, a supply line 34b for feeding water and/or methyl acetate is connected. A high water concentration zone is formed by supplying water and/or methyl acetate through the supply line 34b and by maintaining the water concentration and methyl acetate concentration of a feeding liquid to be fed into the first distillation column 3 to predetermined ranges (for example, 1 to 3% by weight of water and 3 to 5% by weight of methyl acetate). In the zone, hydrogen iodide is concentrated and allowed to react with methyl acetate to convert into methyl iodide. Thus the first distillation column 3 can be prevented from corrosion. Since hydrogen iodide is concentrated around a water concentration of 5% by weight, hydrogen iodide cannot be concentrated if a zone having such a water concentration is not formed in the distillation column (for example, in the case where the water concentration at the top of the distillation column is less than 5% by weight due to insufficient supply of water). However, hydrogen iodide still existing in the distillation column depending on the equilibrium reaction can be converted into methyl iodide by methyl acetate. Thus, even if a zone having a water concentration of about 5% by weight is not formed, the corrosion can be inhibited. Moreover, the reaction of hydrogen iodide with methyl acetate produces methyl iodide, acetic acid and water to improve the liquid-liquid separation into an aqueous phase (light phase) and an organic phase (heavy phase) in the decanter 4.

As shown in FIG. 2, a supply line 35b, for feeding at least one member selected from the group consisting of methyl acetate, methanol and dimethyl ether, and if necessary water, may be connected to the first distillation column 3 instead of the feed line 22, and at least one member selected from the group consisting of methyl acetate, methanol and dimethyl ether, and if necessary water may be supplied to the column using the supply line 35b to maintain the water and methyl acetate concentrations in the first distillation column 3 to predetermined concentrations (concentrations corresponding to predetermined concentrations of water and methyl acetate in a mixture fed to the first distillation column 3). In this embodiment, the supply line 35b connected to the first distillation column 3 is located at substantially the same height as or above the feed site of the volatile phase component.

Further, an addition line 57a and/or 57b for adding an alkali component is connected to a feed line 36, connected to the second distillation column 5, and/or the second distillation column 5. The addition of the alkali component (an aqueous solution of an alkali such as sodium hydroxide, potassium hydroxide, or lithium hydroxide) through the addition line(s) converts hydrogen iodide into an alkali iodide, resulting in removal of hydrogen iodide.

According to such a process (or production apparatus), since not only hydrogen iodide can be converted into methyl iodide and removed in the first distillation column 3 but also hydrogen iodide can also be removed by the alkali component in the second distillation column 5, acetic acid with a high purity can be produced.

Hereinafter, steps and apparatus for producing acetic acid by carbonylation of methanol will be explained in detail.

[Carbonylation Reaction of Methanol]

In the reaction step (carbonylation reaction step), methanol is allowed to continuously react with carbon monoxide using a catalyst system (a catalyst containing a group 8 metal of the Periodic Table, a co-catalyst, and an accelerator) in the presence of water, thereby being carbonylated continuously.

The catalyst containing a group 8 metal of the Periodic Table may include, for example, a rhodium catalyst and an iridium catalyst (in particular, a rhodium catalyst). The catalyst may be used in the form of a halide (e.g., an iodide), a carboxylate (e.g., an acetate), a salt of an inorganic acid, or a complex (in particular, a form soluble in a liquid reaction medium, e.g., a complex). As the rhodium catalyst, there may be mentioned a rhodium iodide complex (for example, $RhI_3$, $[RhI_2(CO)_4]$, and $[Rh(CO)_2I_2]$), a rhodium carbonyl complex; and others. These metal catalysts may be used singly or in combination. The concentration of the metal catalyst is, for example, about 10 to 5000 ppm (on the basis of weight, the same applies hereinafter) and particularly about 200 to 3000 ppm (e.g., about 500 to 1500 ppm) in the whole liquid phase in the reactor.

As the co-catalyst or the accelerator, an ionic iodide or a metal iodide is employed which is useful for stabilization of the rhodium catalyst and inhibition of side reactions in a low water content. It is sufficient that the ionic iodide (or metal iodide) can produce an iodide ion in the liquid reaction medium. The ionic iodide (or metal iodide) may include, for example, an alkali metal iodide (e.g., lithium iodide, sodium iodide, and potassium iodide). The alkali metal iodide (e.g., lithium iodide) also functions as a stabilizer for the carbonylation catalyst (e.g., a rhodium catalyst). These co-catalysts may be used alone or in combination. Among these co-catalysts, lithium iodide is preferred. In the liquid phase system (liquid reaction medium) in the reactor, the concentration of the co-catalyst (e.g., a metal iodide) is, for example, about 1 to 25% by weight, preferably about 2 to 22% by weight, and more preferably about 3 to 20% by weight in the whole liquid phase.

As the accelerator, methyl iodide is utilized. In the liquid phase system (liquid reaction medium) in the reactor, the concentration of methyl iodide is, for example, about 1 to 20% by weight, preferably about 5 to 20% by weight, and more preferably about 6 to 16% by weight (e.g., about 8 to 14% by weight) in the whole liquid phase.

The reaction mixture usually contains methyl acetate, which is produced by a reaction of acetic acid with methanol. The proportion of methyl acetate may be about 0.1 to 30% by weight, preferably about 0.3 to 20% by weight, and more preferably about 0.5 to 10% by weight (e.g., about 0.5 to 6% by weight) in whole reaction mixture.

The reaction may be carried out, in the absence of a solvent or may usually be carried out in the presence of a solvent. As the reaction solvent, acetic acid, which is a product, is usually employed.

The water content of the reaction system may be a low concentration. The water content of the reaction system may for example be not more than 15% by weight (e.g., about 0.1 to 12% by weight), preferably not more than 10% by weight (e.g., about 0.1 to 8% by weight), more preferably about 0.1 to 5% by weight (e.g., about 0.5 to 3% by weight), and usually about 1 to 15% by weight (e.g., about 2 to 10% by weight) in the whole liquid phase in the reaction system.

The carbon monoxide partial pressure in the reactor may for example be about 2 to 30 atmospheres and preferably about 4 to 15 atmospheres. In the carbonylation reaction, hydrogen is formed (or generated) by a shift reaction between carbon monoxide and water. In order to increase the catalyst activity, hydrogen may be fed to the reactor 1, if necessary. The hydrogen partial pressure in the reaction system may for example be about 0.5 to 250 kPa, preferably about 1 to 200 kPa, and more preferably about 5 to 150 kPa (e.g., about 10 to 100 kPa) in terms of absolute pressure.

The reaction temperature may be, for example, about 150 to 250° C., preferably about 160 to 230° C., and more preferably about 180 to 220° C. Moreover, the reaction pressure (total reactor pressure) may be, for example, about 15 to 40 atmospheres.

The space time yield of acetic acid in the reaction system may be, for example, about 5 mol/Lh to 50 mol/Lh, preferably about 8 mol/Lh to 40 mol/Lh, and more preferably about 10 mol/Lh to 30 mol/Lh.

The catalyst mixture (liquid catalyst mixture) containing the catalyst system and water may be continuously fed to the reactor 1. Moreover, in order to adjust the pressure of the reactor, a vapor component (vent gas) may be withdrawn from the reactor. As described above, the vent gas may be fed to the scrubber system, if necessary, and then a useful component (e.g., methyl iodide, acetic acid) may be collected and separated by adsorption treatment and recycled to the reactor 1, and/or a useful gas component (e.g., carbon monoxide) may be separated and recycled to the reactor 1. Moreover, in order to remove part of the reaction heat, the vapor component (vent gas) from the reactor may be condensation-treated by cooling with a condenser, a heat exchanger or other means. The vapor component may be separated into a condensed component (a condensate containing acetic acid, methyl acetate, methyl iodide, acetaldehyde, water, and others) and a noncondensed component (a gaseous component containing carbon monoxide, hydrogen, and others), and the condensed component may be recycled to the reactor to control the reaction temperature of the reaction system, which is an exothermic reaction system. Moreover, the reactor 1 may be equipped with a heat-removable (or heat-removing) unit or a cooling unit (e.g., a jacket) for controlling the temperature of the reaction. The reactor is not necessarily equipped with a heat-removable or cooling apparatus. The noncondensed component may be recycled to the reactor 1, if necessary.

[Flash Evaporation]

In the flash evaporation step (flasher), the reaction mixture continuously fed from the reactor to the flasher (evaporator or flash distillation column) is separated into a volatile phase component (lower boiling point component, vapor component) and a low-volatile phase component (higher boiling point component, liquid component); wherein the volatile phase component contains acetic acid and methyl iodide, and the low-volatile phase component contains a higher boiling point catalyst component (a metal catalyst component, e.g., a metal catalyst and a metal iodide). The volatile phase component (lower boiling point component, vapor component) corresponds to the above-mentioned mixture.

The flash distillation may usually be carried out with the use of a flash distillation column. The flash evaporation step may be composed of a single step or may be composed of a plurality steps in combination. In the flash evaporation step, the reaction mixture may be separated into a vapor component and a liquid component with heating (thermostatic flash) or without heating (adiabatic flash), or the reaction mixture may be separated by combination of these flash conditions. The flash distillation may be carried out, for example, at a temperature of the reaction mixture of about 80 to 200° C. under a pressure (absolute pressure) of about 50 to 1,000 kPa (e.g., about 100 to 1,000 kPa), preferably about 100 to 500 kPa, and more preferably about 100 to 300 kPa. The formation of by-product(s) or the decrease in the catalyst activity may further be inhibited by lowering the internal temperature and/or pressure of the flash evaporator compared with those of the reactor 1.

Moreover, a portion of the volatile phase component may be recycled to the reactor (for example, as described above, a portion of the volatile phase component is heat-removed and condensed in a condenser or a heat exchanger and then recycled to the reactor).

The volatile phase component contains product acetic acid, in addition, hydrogen iodide, a co-catalyst (such as methyl iodide), methyl acetate, water, by-product(s) (e.g., an aldehyde compound such as acetaldehyde or an aldehyde condensation product, a $C_{3-12}$alkanecarboxylic acid such as propionic acid, and a $C_{6-12}$alkyl iodide such as hexyl iodide), and is fed to a distillation column (splitter column) for collecting acetic acid. The separated higher boiling point catalyst component (low-volatile phase component or metal catalyst component) is usually recycled to the reaction system.

[First Distillation]

The following embodiment explains distillation of the mixture and removal of hydrogen iodide in the first distillation column (distillation in the first distillation column). As far as the distillation is carried out by adjusting the water concentration and methyl acetate concentration in the mixture to predetermined concentrations, this embodiment is also applicable to other distillations (the succeeding distillation in second or third distillation column).

The volatile phase component (mixture) contains hydrogen iodide, water, methyl iodide, acetic acid, and methyl acetate. The water content of the mixture may be not less than an effective amount for forming a high water concentration zone in the distillation column and not more than 5% by weight. When the water content exceeds 5% by weight, a condensed zone of hydrogen iodide is shifted downwardly to a position for feeding the mixture (volatile phase component) to the distillation column, and thus hydrogen iodide cannot be removed effectively. The zone having a high water concentration in the distillation column is shifted upwardly to the column top direction, and hydrogen iodide cannot be removed effectively. According to the present invention, the condensed zone of hydrogen iodide can be formed above the feed position by adjusting the water concentration in the fed mixture to not more than 5% by weight, and hydrogen iodide can be effectively removed due to methyl acetate (which is concentrated above the feed position) in the mixture, so that the corrosion can be inhibited. Moreover, even if the condensed zone of hydrogen iodide is not formed in the distillation column, hydrogen iodide existing in the distillation column according to the equilibrium reaction is converted by methyl acetate, so that the corrosion can be inhibited.

The water content of the mixture may usually be about 0.5 to 4.5% by weight (e.g., about 1 to 4.3% by weight) and preferably about 1.2 to 4% by weight (e.g., about 1.5 to 3.5% by weight). According to the present invention, a high water concentration zone inside the distillation column can be formed above a position for feeding the mixture (volatile phase component) to the distillation column. Thus, hydrogen iodide is allowed to react with methyl acetate (and also methanol in the mixture and by-product methanol) at the high water concentration zone to produce methyl iodide and acetic acid.

The methyl acetate concentration in the mixture can be selected within the range from not less than an effective amount for converting hydrogen iodide into methyl iodide in the distillation column to not more than 9% by weight (0.5 to 9% by weight). When the methyl acetate concentration exceeds 9% by weight, the condensate of the overhead shows a low liquid-liquid separation. The methyl acetate concentration in the mixture may usually be about 0.5 to 8% by weight (e.g., about 0.5 to 7.5% by weight), preferably about 0.7 to 6.5% by weight (e.g., about 1 to 5.5% by weight), and more preferably 1.5 to 5% by weight (e.g., about 2 to 4.5% by weight), or may be about 0.5 to 7.2% by weight. The mixture representatively contains about 1 to 4.3% by weight (e.g., about 1.3 to 3.7% by weight) of water; and about 0.5 to 7.5% by weight (e.g., about 0.8 to 7.5% by weight), preferably about 1.2 to 5% by weight (e.g., about 1.7 to 4.5% by weight) of methyl acetate.

The methyl iodide content of the mixture may for example be about 25 to 50% by weight (e.g., about 27 to 48% by weight), preferably about 30 to 45% by weight (e.g., about 32 to 43% by weight), and more preferably about 35 to 40% by weight (e.g., about 36 to 39% by weight).

When the distillation is carried out continuously, the methyl acetate concentration in the mixture may usually be about 0.07 to 1.2 mol/L (about 0.5 to 9% by weight), preferably about 0.1 to 1.0 mol/L, and more preferably about 0.3 to 0.8 mol/L. Moreover, the water concentration in the mixture may be about 0.28 to 2.8 mol/L (about 0.5 to 5% by weight), preferably about 0.56 to 2.5 mol/L (about 1 to 4.5% by weight), and more preferably about 0.83 to 2.2 mol/L (about 1.5 to 4% by weight).

According to the present invention, since hydrogen iodide can be removed efficiently, the hydrogen iodide content of the mixture is not particularly limited to a specific one. For example, the hydrogen iodide content may be about 10 to 30000 ppm. The hydrogen iodide content of the mixture (volatile phase component) produced by the methanol carbonylation reaction may be about 100 to 10000 ppm, preferably about 200 to 7500 ppm, and more preferably about 300 to 6000 ppm (e.g., about 500 to 5000 ppm) on the basis of weight. Moreover, the acetic acid content of the mixture is not particularly limited to a specific one, and may for example be about 30 to 70% by weight (e.g., about 35 to 75% by weight), preferably about 40 to 65% by weight (e.g., about 45 to 62% by weight), and more preferably about 50 to 60% by weight (e.g., about 54 to 58% by weight).

The mixture (volatile phase component) may further contain dimethyl ether. The concentration of dimethyl ether can for example be selected from the range of 0.15 to 3% by weight, and may usually be about 0.15 to 2.5% by weight (e.g., about 0.17 to 2.3% by weight), preferably about 0.2 to 2% by weight (e.g., about 0.3 to 1.7% by weight), and more preferably about 0.5 to 1.5% by weight. Most of the remainder (residual component) of the mixture is often methanol. As described above, the mixture (volatile phase component) produced by the methanol carbonylation reaction practically contains a trace of an impurity (e.g., acetaldehyde, an aldehyde condensation product, a higher boiling point carboxylic acid such as propionic acid, and a $C_{6-12}$alkyl iodide).

The total amount of each component in the mixture (volatile phase component) is 100% by weight. Moreover, although the mixture (volatile phase component) may form a vapor phase (or distillation atmosphere), the amount and concentration of the above-mentioned each component indicate those of the mixture (volatile phase component) in the form of a liquid, for example, a condensate (for example, a liquefied condensate formed by cooling at 20 to 25° C.) obtained by cooling and condensing a vapor phase mixture (a volatile phase component forming a vapor phase).

The water concentration and the methyl acetate concentration in the mixture may be adjusted by feeding (or supplying) water and/or methyl acetate. The mixture containing a predetermined concentration, of water and that of methyl acetate may be directly distilled without adjusting the water concentration and the methyl acetate concentration. Moreover, water and/or methyl acetate may be fed (or supplied or added) to the mixture (volatile phase component) or in the distillation atmosphere (the distillation atmosphere in the distillation column) of the volatile phase component (mixture) to adjust a water concentration to not more than 5% by weight and a methyl acetate concentration to 0.5 to 9% by weight for distilling the volatile phase component. The water and/or methyl acetate can be fed (or supplied) to the feed line 22 or the first distillation column by using various lines connected to the first distillation column or a new line.

The adjustment (or control) of the water concentration and the methyl acetate concentration can be conducted by analyzing or detecting water and methyl acetate concentrations in the mixture (volatile phase component) introduced into the distillation column, and based on the results, and adjusting the ratio of the components of the mixture in the distillation column, or a unit or line (which is for supplying a fluid to the distillation column) by using a controller (control unit); or can also be conducted by supplying or adding water and/or methyl acetate. The unit for supplying the fluid to the distillation column may include the reactor or flasher which is located upstream of the distillation column, a decanter for feeding a condensate to the distillation column, and others.

The distillation atmosphere (the distillation atmosphere in the distillation column) of the mixture (volatile phase component) can be formed in an appropriate place inside the distillation column. In order to convert hydrogen iodide effectively, it is preferred to form the distillation atmosphere at the same height as or above the feed site of the volatile phase component.

Further, to the volatile phase component as the mixture, or to the distillation atmosphere of the volatile phase component as the mixture, at least one member selected from the group consisting of methyl acetate, methanol and dimethyl ether (a methanol source) and if necessary water may be added to form a volatile phase component (mixture) having adjusted water and methyl acetate concentrations for distilling the volatile phase component (mixture). The amounts of methyl acetate and water to be added are as described above. Moreover, the amount of methanol to be added may for example be about 0.01 to 3.8 parts by weight (e.g., about 0.1 to 3 parts by weight), preferably about 0.1 to 2.5 parts by weight (e.g., about 0.2 to 2 parts by weight), and more preferably about 0.2 to 1.5 parts by Weight (e.g., about 0.5 to 1.5 parts by weight) relative to 100 parts by weight of the mixture (volatile phase component). The amount of dimethyl ether to be added is an amount to form the dimethyl ether concentration in the mixture as described above. The amount of dimethyl ether to be added may for example be about 0.01 to 2.7 parts by weight (e.g., about 0.03 to 2 parts by weight), preferably about 0.05 to 1.5 parts by weight (e.g., about 0.07 to 1.3 parts by weight), and more preferably, about 0.1 to 1 parts by weight (e.g., about 0.2 to 0.8 parts by weight) relative to 100 parts by weight of the mixture (volatile phase component).

In the splitter column (first distillation column), the mixture (volatile phase component) is distilled (in particular, continuously distilled) and separated into an overhead containing a lower boiling point component such as methyl iodide (including methyl iodide produced by a reaction of methyl acetate with methanol), and a side cut stream or bottom stream containing acetic acid, and acetic acid is collected. In the distillation column, usually, a volatile phase component is separated as a vapor overhead (usually containing methyl iodide, methyl acetate, acetaldehyde, water, and others); a side cut stream (side stream) containing acetic acid is separated as a liquid form by side-cut; and a bottom stream (bottom liquid stream or higher boiling point component, containing acetic acid, water, propionic acid, entrained metal catalyst component, a metal halide, and others) is separated as a liquid form.

This distillation can significantly reduce the concentration of hydrogen iodide in the second overhead and the side cut stream. In particular, the side cut stream (crude acetic acid stream) having a significantly decreased concentration of hydrogen iodide can be obtained. The hydrogen iodide concentration in the side cut stream may for example be about 1 to 350 ppm, preferably about 2 to 300 ppm, and more preferably about 3 to 250 ppm.

The position of the feed line 22 connected (or joined) to the first distillation column 3 (the feed site of the volatile phase component) is not particularly limited to a specific one. For example, the position of the feed line may be in an upper part, a middle part, or a lower part of the distillation column. The mixture is practically fed to the distillation column from an intermediate or lower position of the distillation column in height. Specifically, the connecting (or joining) position of the feed line 22 (the feed site of the volatile phase component) is practically located at an intermediate or lower position of the first distillation column 3. Since feeding of the mixture in such a manner can form a high water concentration zone between at or above an intermediate position of the distillation column and below thew reflux line 42, thus the efficient contact of hydrogen iodide with methyl acetate (and methanol) can be increased, which can improve the hydrogen iodide removal efficiency. Moreover, the side cut stream (crude acetic acid stream) from the first distillation column 3 may be withdrawn from any of an upper part, a middle part, and a lower part of the distillation column, for example, the side cut stream may be withdrawn from the same height as the position (feed site) of the feed line 22 joined to the first distillation column 3 or from above or below the position (feed site) thereof. The side cut stream is usually withdrawn from a middle part or a lower part (lower part to middle part) of the distillation column, for example, a site below the connecting position of the feed line 22 (the feed site of the volatile phase component) (e.g., a site between above the column bottom and below the connecting position (feed site) of the feed line 22).

Moreover, as shown in FIG. 2, the supply line 35b connected to the first distillation column 3 may be located at the same height position as the feed site of the volatile phase component from the feed line 22, or may be located below or above the feed site of the volatile phase component. The supply line 35b is usually located at the same height position as the feed site of the volatile phase component or above the feed site of the volatile phase component.

The bottom stream may be removed (discharged) from the bottom or lower part of the distillation column. Since the bottom stream contains a useful component such as a metal catalyst component or acetic acid, the bottom stream may be recycled to the reactor (or reaction step) or the flash evaporation step, as described above. Moreover, the bottom stream may be recycled to the reaction system or others through a storage vessel having a buffering function. The bottom stream may be fed to the second distillation column 5 for removing a high boiling point impurity such as propionic acid.

As the splitter column (distillation column), there may be used a conventional distillation column, for example, a plate column, a packed column, and a flash distillation column. A distillation column such as a plate column or a packed column may be usually employed. The material of (or for forming) the distillation column is not limited to a specific one, and a glass, a metal, a ceramic, or others can be used. In usual, a distillation column made of a metal is used practically.

For the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde in the distillation column, the theoretical number of plates may be about 10 to 80, preferably about 20 to 60, and more preferably about 25 to 50. Further, in the distillation column, the reflux ratio may be selected from, for example, about 0.5 to 3,000, and preferably about 0.8 to 2,000 depending on the above-mentioned theoretical number of plates, or may be reduced by increasing the theoretical number of plates.

The distillation temperature and pressure in the splitter column (distillation column) may suitably be selected. For example, in the distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C. The temperature of the column top can be set to a temperature lower than the boiling point of acetic acid depending on the inner pressure of the column (for example, lower than 118° C., preferably not higher than 117° C.). The temperature of the column bottom can be set to a temperature higher than the boiling point of acetic acid depending on the inner pressure of the column (for example, not lower than 130° C., preferably not lower than 135° C.).

The overhead from the first distillation column contains methyl iodide, acetaldehyde, and in addition, methyl acetate, water, methanol, acetic acid, an aldehyde or a carbonyl impurity (such as crotonaldehyde or butyraldehyde), a $C_{2-12}$alkyl iodide, a $C_{3-12}$alkanecarboxylic acid, and others.

[Condensation and Liquid-Liquid Separation]

The overhead from the first distillation column is cooled and condensed in a cooling unit (condenser), and the resulting condensate of the overhead can clearly be separated into an aqueous phase (light phase, upper phase) and an organic phase (heavy phase, lower phase) in a liquid-separating unit (decanter). In this manner, the separability of the overhead into the aqueous phase (light phase) and the organic phase (heavy phase) can be improved.

As described above, methyl acetate has a miscibility with both aqueous phase (light phase) and organic phase (heavy phase). The liquid-liquid separation decreases at a higher concentration of methyl acetate. Thus, the concentration of methyl acetate in the separated organic phase (heavy phase, lower phase) may be about 0.5 to 15% by weight (e.g., about 1 to 15% by weight), preferably about 1.5 to 14% by weight (e.g., about 2 to 10% by weight), and more preferably about 2 to 8% by weight (e.g., about 2.5 to 7% by weight); and the concentration of methyl acetate in the aqueous phase (light phase, upper phase) may be about 0.2 to 8.5% by weight (about 0.4 to 8% by weight), preferably about 0.5 to 7.5% by weight (e.g., about 0.6 to 6% by weight), and more preferably about 0.7 to 5% by weight (e.g., about 0.8 to 4.5% by weight) or may be about 0.4 to 8% by weight (e.g., about 1 to 5% by weight).

Moreover, the liquid-liquid separation into the aqueous phase and the organic phase is sometimes influenced by other components. In the separated organic phase (heavy phase), the concentration of methyl iodide may for example be about 75 to 98% by weight (e.g., about 76 to 98% by weight) and preferably about 78 to 97% by weight (e.g., about 80 to 96% by weight), and the concentration of acetic acid may be about 1 to 10% by weight (e.g., about 2 to 8% by weight) and preferably about 2.5 to 7.5% by weight (e.g., about 3 to 7.5% by weight). The concentration of water in the organic phase (heavy phase) is usually not more than 1% by weight. Moreover, in the aqueous phase (light phase), the concentration of water may be about 50 to 90% by weight (e.g., about 55 to 90% by weight) and preferably about 60 to 85% by weight (e.g., about 65 to 80% by weight), and the concentration of acetic acid may be about 10 to 40% by weight (e.g., 12 to 35% by weight) and preferably about 13 to 30% by weight. The sum of the percentage of all components in the organic phase (heavy phase) is 100% by weight, and that in the aqueous phase (light phase) is 100% by weight.

The concentration of hydrogen iodide in the aqueous phase (light phase) is higher than that in the organic phase (heavy phase). For example, the concentration of hydrogen iodide in the organic phase (heavy phase) is about not more than 70 ppm (for example, trace to 60 ppm), while the concentration of hydrogen iodide in the aqueous phase (light phase) is about 10 to 1000 ppm (e.g., about 50 to 800 ppm). For that reason, feeding of the aqueous phase (light phase) to the third distillation column can improve the hydrogen iodide removal efficiency. Moreover, feeding of both of the aqueous phase (light phase) and the organic phase (heavy phase) to the third distillation column can further improve the hydrogen iodide removal efficiency.

In an example shown in the figure, the organic phase (heavy phase) is recycled to the reactor 1, and the aqueous phase (light phase) is recycled to the first distillation column 3 for reflux. The organic phase (heavy phase) and/or the aqueous phase (light phase) may be recycled to the reactor 1 or may be recycled to the first distillation column 3.

[Second Distillation]

The first side cut stream (liquid crude acetic acid) usually contains acetic acid, and other components (e.g., methyl iodide, methyl acetate, water, and hydrogen iodide) which remain without separation in the first distillation column. The side cut stream (liquid crude acetic acid) from the first distillation column is usually further distilled (or dehydrated) in the second distillation column, and separated into an overhead (low-boiling content) from the column top, a bottom stream (high-boiling component such as a $C_{3-12}$alkanecarboxylic acid including propionic acid) from the column bottom, and a side cut stream (purified acetic acid) from the side, and product acetic acid may be obtained as the side cut stream.

In the second distillation column, removal of hydrogen iodide by an alkali component is not necessarily needed. As described above, water and hydrogen iodide usually remain in the first side cut stream (liquid crude acetic acid). The distillation of the first side cut stream (liquid crude acetic acid) condenses hydrogen iodide in the second distillation column. Moreover, hydrogen iodide is also produced by a reaction of methyl iodide with water as shown in the above-mentioned equation (3). Thus, not only hydrogen iodide together with water is concentrated in the upper part of the second distillation column, but also hydrogen iodide is liable to be produced by a reaction of methyl iodide with water in the upper part of the second distillation column. Accordingly, it is preferable to add an alkali component for removing hydrogen iodide and for obtaining acetic acid with a further high purity. Specifically, in the second distillation column, the first side cut stream may be distilled in the presence of an alkali component (for example, an alkali metal hydroxide such as potassium hydroxide), or a mixture containing the first side cut stream and the alkali component may be distilled.

The alkali component (alkaline aqueous solution) can be added to the side cut stream or the distillation column by using various routes connected to the distillation column or a new route. In the example shown in the figure, the alkali component may be added through at least one line of addition lines 57a and 57b. Moreover, the position of the feed line 36 (or addition part) and that of an addition line 57b to the second distillation column 5 are not particularly limited. Each position may be located at the middle part of the second distillation column 5 or below or above the middle part thereof. In usual, the position of addition by the feed line 36 is practically located at or below the middle part of the second distillation column 5; the position of addition by the addition line 57b is practically located at or above the middle part of the second distillation column 5. The addition of the alkali component according to such an embodiment allows hydrogen iodide to be efficiently neutralized prior to movement or migration of hydrogen iodide to the column top of the second distillation column, even if the alkali component (non-volatile alkali component) is easily moved to the lower part of the distillation column. Thus, the concentration of hydrogen iodide at all over the distillation column including not only the lower part of the distillation column but also the upper part of the distillation column can be efficiently inhibited.

In the second distillation column, the first side cut stream may be distilled in the presence of a reactive component having a boiling point lower than that of acetic acid and converting hydrogen iodide into methyl iodide (at least one methanol or a derivative thereof, selected from the group consisting of methanol, dimethyl ether and methyl acetate, particularly, methyl acetate) in addition to the alkali component. The methanol or the derivative thereof (particularly, methyl acetate) may be contained in the first side cut stream, and is preferably added via (through) the addition lines 57a, 57b, and other routes. As described above, the reaction of methyl iodide with water easily occurs in the upper part of the distillation column, while the alkali component is easily moved to the lower part of the distillation column. Thus, the amount of the alkali component existing in the upper part of the distillation column sometimes decreases. The addition of the methanol or the derivative thereof, which has a low boiling point, in combination of the alkali component can inhibit concentration of hydrogen iodide in the upper part of the distillation column with more certainty, and can remove hydrogen iodide by converting hydrogen iodide into a metal iodide or methyl iodide.

The water content of the first side cut stream (liquid crude acetic acid) is usually about 0.3 to 5% by weight (e.g., about 0.5 to 4% by weight, preferably about 0.7 to 3.5% by weight, and more preferably about 1 to 3% by weight), and the methyl acetate content thereof is about 0.1 to 3% by weight (e.g., about 0.2 to 2.5% by weight, preferably about 0.5 to 2% by weight, and more preferably about 0.7 to 1.5% by weight). The water concentration and methyl acetate concentration of the first side cut stream (liquid crude acetic acid) can also be used for removing hydrogen iodide. Specifically, water and/or acetic acid may be supplied to the side cut stream or the second distillation column, together with the addition of the alkali component or instead of the addition of the alkali component, to adjust the water concentration and the methyl acetate concentration, for converting hydrogen iodide into methyl iodide and for removing hydrogen iodide in the same manner as the first distillation. In this case, in order to increase the dehydration efficiency, supply of methyl acetate without addition of water is advantageous.

The overhead from the column top or upper part of the second distillation column 5 is usually condensed in condenser C4, and the resulting condensate may be returned to the reactor 1 and/or the second distillation column 5. When the condensate has a predetermined amount of water and can form separated liquid phases, the condensate may be separated into an aqueous phase and an organic phase in the same manner as described above and recycled to the reactor 1, the first distillation column 3 and/or the second distillation column 5. The water may be separated as a low-boiling component in the second distillation column 5, and the separated water may be fed to the reactor 1 or a water extractor 7. The higher boiling point fraction (second higher boiling point component) such as a high-boiling component (e.g., propionic acid) may be withdrawn from the column bottom or the lower part of the column, and if necessary may be returned to the reactor 1 or discharged out of the system. Moreover, if necessary, the second side cut stream (purified acetic acid stream) may further be subjected to a purification step such as distillation.

[Separation and Removal of Impurity]

The embodiment of FIG. 1 shows a process provided with a separation and removal system for removing an impurity (a third distillation column 6, a water extraction column (water extractor) 7 and a fourth distillation column 8). These separation and removal systems are not necessarily needed. Moreover, for the separation and removal of the impurity, it is sufficient that the condensate in the decanter 4 is subjected to the separation and removal system. In the case where the condensate is separated into two liquid layers (two liquid phases), the aqueous phase (light phase) and/or the organic phase (heavy phase) may be subjected to the separation and removal system. Further, the separation and removal system may adopt various separation and removal processes without limitation to the above-mentioned process.

[Vent Gas]

The noncondensed component (vent gas component) from the condenser may be released out of the system. If necessary, the noncondensed component may be recycled to the reactor 1 directly, or may be fed to the scrubber system to separate and collect a useful component (such as methyl iodide or acetic acid) from the noncondensed component, and the useful component may optionally be recycled to the reactor 1. For the scrubber system, various separation and purification processes, such as PSA (pressure swing adsorption, pressure swing adsorption) method, may be used.

EXAMPLES

The following examples are intended to describe this invention in further detail and should by no means be interpreted as defining the scope of the invention.

Comparative Example 1

In a continuous production process for acetic acid shown in FIG. 2, methanol was allowed to react with carbon monoxide in a carbonylation reactor, the reaction mixture obtained from the reactor was continuously fed to a flasher and separated into a low-volatile phase component (a bottom component at least containing a rhodium catalyst, lithium iodide, acetic acid, methyl acetate, methyl iodide, water and hydrogen iodide) and a volatile phase component (a liquefied gas component, liquid temperature: 135° C.) by a flash distillation. The volatile phase component was fed to a first distillation column. Supply lines 34b and 35b were not used. Moreover, the volatile phase component included 38.2% by weight of methyl iodide (MeI), 0.3% by weight of methyl acetate (MA), 6.5% by weight of water ($H_2O$), 5000 ppm (on the basis of weight) of hydrogen iodide (HI), and 54.5% by weight of acetic acid (wherein the acetic acid content was calculated by subtracting the sum total of components other than acetic acid from 100% by weight, the same applies hereinafter).

To the first distillation column (number of plates: 20, charging plate: 2nd plate from bottom), 100 parts by weight of the volatile phase component was fed, distilled at a gauge pressure of 150 KPA, a column bottom temperature of 140° C., a column top temperature of 115° C. and a reflux ratio of a light phase of 3, and liquid-liquid separated by cooling and decantation to form an aqueous phase and an organic phase. The aqueous phase (light phase, 5 parts by weight) and the organic phase (heavy phase, 38 parts by weight) were recycled to the reactor. The composition (formulation) of the column top of the first distillation column (the composition of the overhead) was as follows: 63.8% by weight of methyl iodide (MeI), 0.6% by weight of methyl acetate (MA), 23.3% by weight of water ($H_2O$), 440 ppm of hydrogen iodide (HI), and 12.3% by weight of acetic acid. The composition of the aqueous phase (light phase) was as follows: 2.6% by weight of methyl iodide (MeI), 0.3% by weight of methyl acetate (MA), 67.0% by weight of water ($H_2O$), 900 ppm of hydrogen iodide (HI), and 30.0% by weight of acetic acid. The composition of the organic phase (heavy phase) was as follows: 96% by weight of methyl iodide (MeI), 0.7% by weight of methyl acetate (MA), 0.3% by weight of water ($H_2O$), 200 ppm of hydrogen iodide (HI), and 3.0% by weight of acetic acid.

From the side-cut of first distillation column (side-cut plate: 4th from bottom) and the column bottom, a side cut stream containing acetic acid and a bottom stream containing an entrained catalyst were withdrawn in a proportion of 54 parts by weight and a proportion of 3 parts by weight, respectively. The bottom stream was recycled to the reaction system. The side cut stream was fed to a second distillation column for dehydration and purification. The composition of the side cut stream was as follows: 2.9% by weight of MeI, 0.03% by weight of MA, 5.3% by weight of $H_2O$, 970 ppm of HI, and 90.8% by weight of acetic acid.

The term "parts by weight" of a fluid (e.g., a volatile phase component, an aqueous phase (light phase) and an organic phase (heavy phase), a side cut stream and a bottom stream) indicates a flow rate per hour (the same applies hereinafter).

In the continuous reaction process, the following test pieces were placed on 3nd plate from bottom (which was the first plate above the charging plate of the first distillation column) undermost plate of the column (which was the first plate below the charging plate), and 19th plate from bottom (which was the column top). After leaving for 100 hours, each test piece was examined for a corrosion test. The weight of each test piece before and after the corrosion test was measured to determine a corrosion amount. Based on the measured corrosion amount (decrease in weight) and the area of the test piece, the corrosion rate (decrease in thickness) of the test piece per year was converted into a thickness (mm) and shown in the unit "mm/Y".

[Test Piece]
HB2: manufactured by Oda Kaki Co., Ltd, HASTELLOY B2 (nickel-based alloy)
HC: manufactured by Oda Koki Co., Ltd, HASTELLOY C (nickel-based alloy)
SUS316L: manufactured by Umetoku Inc., SUS 316 Low Carbon (stainless steel)

Comparative Example 2

The corrosion test was carried out in the same manner as in Comparative Example 1 except that the charging mixture (volatile phase component) was adjusted to a water concentration of 4% by weight and then fed to the first distillation column and that the reflux ratio in the first distillation column and the amounts of the light phase and the heavy phase recycled to the reaction system were changed depending on the water concentration.

The composition of the volatile phase component was as follows: 38.5% by weight of MeI, 0.3% by weight of MA, 4.0% by weight of $H_2O$, 5000 ppm of HI, and 56.7% by weight of acetic acid. Moreover, the distillation was carried out at a light phase reflux ratio of 5, and the light phase (3.3 parts by weight) and the heavy phase (38.5 parts by weight) were recycled to the reaction system. The composition of the column top of the first distillation column (the composition of the overhead) was as follows: 64.3% by weight of MeI, 0.6% by weight of MA, 23.3% by weight of $H_2O$, 470 ppm of HI, and 11.8% by weight of acetic acid. The composition of the aqueous phase (light phase) was as follows: 2.6% by weight of MeI, 0.3% by weight of MA, 68.0% by weight of $H_2O$, 1200 ppm of HI, and 29.0% by weight of acetic acid. The composition of the organic phase (heavy phase) was as follows: 96% by weight of MeI, 0.7% by weight of MA, 0.3% by weight of $H_2O$, 90 ppm of HI, and 3.0% by weight of acetic acid. From the first distillation column, a side cut stream containing acetic acid and a bottom stream were withdrawn in a proportion of 55.2 parts by weight and a proportion of 3 parts by weight, respectively. The composition of the side cut stream was as follows: 2.6% by weight of MeI, 0.04% by weight of MA, 2.8% by weight of $H_2O$, 820 ppm of HI, and 93.6% by weight of acetic acid. The composition of the bottom stream was as follows: 0% by weight of MeI, 0.03% by weight of MA, 2.6% by weight of $H_2O$, 800 ppm of HI, and 97.1% by weight of acetic acid. The column top temperature of the first distillation column was 115° C., and the column bottom temperature thereof was the same as that in Comparative Example 1.

Comparative Example 3

The corrosion test was carried out in the same manner as in Comparative Example 2 except that the charging mixture (volatile phase component) was adjusted to a methyl acetate concentration of 10% by weight and then fed to the first distillation column and that the reflux ratio in the first distillation column and the amounts of the light phase and the heavy phase recycled to the reaction system were changed depending on the methyl acetate concentration. However, the charging mixture (volatile phase component) had a poor liquid-liquid separation into the light phase and the heavy phase. These phases formed a mixed phase or one phase, and the results made the operation unstable after several hours. Thus it was impossible to operate the process operation for a long period of time.

Examples 1 to 4

The corrosion test was carried out in the same manner as in Comparative Example 1 except that the charging mixture (volatile phase component) having appropriate methyl acetate and water concentrations in each Example is fed to the first distillation column and that the reflux ratio in the first distillation column and the amounts of the light phase and the heavy phase recycled to the reaction system were changed depending on the methyl acetate and water concentrations.

Operation conditions in each of Examples and Comparative Examples are shown in Table 1. The results of the corrosion test are shown in Table 2. The unit of numerical values in Table 2 is the corrosion rate "mm/Y".

TABLE 1

|  |  | Parts by weight (ppm for HI) | Comparative Examples | | | Examples | | | |
|---|---|---|---|---|---|---|---|---|---|
|  |  |  | 1 | 2 | 3 | 1 | 2 | 3 | 4 |
| Feed | Flow rate |  | 100 | 100 | 100 | 100 | 100 | 100 | 100 |
|  | MeI |  | 38.2 | 38.5 | 38 | 38 | 38.5 | 37 | 36 |
|  | MA |  | 0.3 | 0.3 | 10 | 0.5 | 1 | 4.2 | 7.2 |
|  | Water |  | 6.5 | 4 | 4 | 4 | 4 | 1.2 | 2 |
|  | HI |  | 5000 | 5000 | 200 | 4000 | 2000 | 600 | 300 |
|  | AC |  | 54.5 | 56.7 | 47.6 | 57.1 | 56.3 | 57.4 | 54.7 |
| Side-cut | Flow rate |  | 54 | 55.2 | 43.5 | 55.2 | 55.2 | 54.2 | 51.6 |
|  | MeI |  | 2.9 | 2.6 | 2.3 | 1.7 | 4.0 | 3.1 | 2.3 |
|  | MA |  | 0.03 | 0.04 | 2.6 | 0.06 | 0.21 | 1.26 | 1.6 |
|  | Water |  | 5.3 | 2.8 | 2.8 | 2.8 | 2.7 | 0.7 | 1.2 |
|  | HI |  | 970 | 820 | trace | 290 | 90 | 20 | 5 |
|  | AC |  | 90.8 | 93.6 | 91.5 | 94.7 | 92.7 | 94.5 | 94.8 |
| Column top | Flow rate |  | 58 | 58.3 | 68.5 | 58.3 | 58.3 | 49.2 | 62.2 |
|  | MeI |  | 63.8 | 64.3 | 54.9 | 64.3 | 63.3 | 72.2 | 57.4 |
|  | MA |  | 0.56 | 0.56 | 14.79 | 0.93 | 1.76 | 7.63 | 12.36 |
|  | Water |  | 23.3 | 23.3 | 22.6 | 23.3 | 23.4 | 11.9 | 20.9 |
|  | HI |  | 440 | 470 | trace | 240 | 70 | 70 | 7 |
|  | AC |  | 12.3 | 11.8 | 7.8 | 11.5 | 11.5 | 8.2 | 9.4 |
| Column bottom | Flow rate |  | 3 | 3 | 3 | 3 | 3 | 3 | 3 |
|  | MeI |  | 0.0 | 0.0 | 0.0 | 0.0 | 0.2 | 0.1 | 0.0 |
|  | MA |  | 0.03 | 0.03 | 0.17 | 0.17 | 0.17 | 1.20 | 1.18 |
|  | Water |  | 5.3 | 2.6 | 2.6 | 2.6 | 2.6 | 0.6 | 1.14 |
|  | HI |  | 440 | 470 | 300 | 290 | 90 | 20 | 5 |
|  | AC |  | 94.6 | 97.3 | 96.3 | 97.2 | 97.0 | 98.1 | 97.7 |
| Reflux | Flow rate |  | 15 | 16.5 | 15 | 16.5 | 16.5 | 6.4 | 16.8 |
|  | MeI |  | 2.6 | 2.6 | 4 | 2.6 | 3.5 | 3.5 | 5.1 |
|  | MA |  | 0.3 | 0.3 | 8.3 | 0.5 | 0.9 | 4.3 | 7.9 |
|  | Water |  | 67 | 68 | 85 | 68 | 68.2 | 79 | 69.1 |
|  | HI |  | 900 | 1200 | trace | 710 | 250 | 70 | 20 |
|  | AC |  | 30.01 | 28.98 | 2.7 | 28.83 | 27.4 | 13.18 | 17.9 |
| Upper phase (light phase) | Flow rate |  | 5 | 3.3 | 3.0 | 3.3 | 3.3 | 0.80 | 1.40 |
|  | MeI |  | 2.6 | 2.6 | 4 | 2.6 | 3.5 | 3.5 | 5.1 |
|  | MA |  | 0.3 | 0.3 | 8.3 | 0.5 | 0.9 | 4.3 | 7.9 |
|  | Water |  | 67 | 68 | 85 | 68 | 68.2 | 79 | 69.1 |
|  | HI |  | 900 | 1200 | trace | 710 | 250 | 70 | 20 |
|  | AC |  | 30.0 | 29.0 | 2.7 | 28.8 | 27.4 | 13.2 | 17.9 |
| Lower phase (heavy phase) | Flow rate |  | 38 | 38.5 | 50.5 | 38.5 | 38.5 | 42 | 44 |
|  | MeI |  | 96 | 96 | 73 | 96 | 94 | 84 | 79 |
|  | MA |  | 0.7 | 0.7 | 17.1 | 1.15 | 2.2 | 8.2 | 14.2 |
|  | Water |  | 0.3 | 0.3 | 0.3 | 0.3 | 0.4 | 0.4 | 0.9 |
|  | HI |  | 110 | 90 | trace | 50 | 40 | trace | trace |
|  | AC |  | 3.0 | 3.0 | 9.6 | 2.5 | 3.4 | 7.4 | 5.9 |

TABLE 2

| Position of test piece | Test piece | Comparative Examples | | | Examples | | | |
|---|---|---|---|---|---|---|---|---|
|  |  | 1 | 2 | 3 | 1 | 2 | 3 | 4 |
| Column top (19th plate) | Zr | 0.00 | 0.00 | — | 0.00 | 0.00 | 0.00 | 0.00 |
|  | HB2 | 0.1 | 0.09 | — | 0.06 | 0.05 | 0.02 | 0.01 |
|  | HC | 0.22 | 0.18 | — | 0.12 | 0.09 | 0.05 | 0.02 |
|  | SUS | 0.54 | 0.3 | — | 0.23 | 0.18 | 0.06 | 0.03 |
| Charging plate + 1 | 316L Zr | 0.00 | 0.00 | — | 0.00 | 0.00 | 0.00 | 0.00 |
|  | HB2 | 0.23 | 0.18 | — | 0.07 | 0.05 | 0.01 | 0.01 |
|  | HC | 0.51 | 0.42 | — | 0.18 | 0.09 | 0.04 | 0.02 |
|  | SUS 316L | Not test | Not test | — | 0.51 | 0.22 | 0.06 | 0.04 |
| Bottom (Charging plate − 1) | Zr | 0.00 | 0.00 | — | 0.00 | 0.00 | 0.00 | 0.00 |
|  | HB2 | 0.27 | 0.09 | — | 0.06 | 0.06 | 0.04 | 0.02 |
|  | HC | 0.6 | 0.21 | — | 0.11 | 0.1 | 0.05 | 0.03 |

TABLE 2-continued

| Position of test piece | Test piece | Comparative Examples | | | Examples | | | |
|---|---|---|---|---|---|---|---|---|
| | | 1 | 2 | 3 | 1 | 2 | 3 | 4 |
| | SUS 316L | Not test | 0.6 | — | 0.4 | 0.24 | 0.08 | 0.05 |

Comparative Example 3 failed to operate the apparatus stably, and the corrosion could not be evaluated.

As apparent from Table 1 and Table 2, in Comparative Example 1, corrosion developed in the whole distillation column. In Comparative Example 2, since a concentrated zone of hydrogen iodide was transferred above the charging plate due to a lower concentration of water in the charging mixture (volatile phase component), the corrosiveness of the bottom was decreased; while due to a low concentration of methyl acetate in the charging mixture (volatile phase component), corrosion developed above the charging plate. In Comparative Example 3, although the corrosiveness of the whole column was improved, the condensate (withdrawn liquid) of the overhead from the column top had a markedly low liquid-liquid separation, so that the distillation column could not be operated stably over a long period of time. In Example 1, due to a high concentration of methyl acetate in the charging mixture (volatile phase component), methyl acetate allowed to effectively react with hydrogen iodide. In particular, the test piece "HB2" showed a relatively excellent corrosion resistance in the whole column. In Example 2, due to a higher concentration of methyl acetate in the charging mixture (volatile phase component), the test piece "HB2" showed a substantially complete corrosion-resisting level (corrosion rate: not more than 0.05 mm/Y). In Examples 3 and 4, due to a further higher concentration of methyl acetate in the charging mixture (volatile phase component), each of the test pieces "HB2", "HC" and "SUS316L" showed a complete corrosion resistance independent of the change of the water concentration.

INDUSTRIAL APPLICABILITY

According to the present invention, since the water concentration and the methyl acetate concentration in the distillation column are adjusted or controlled, the overhead from the distillation column can be condensed to form an aqueous phase and an organic phase while preventing corrosion of the distillation column due to hydrogen iodide. Thus, the present invention advantageously allows industrial continuous production of acetic acid.

DESCRIPTION OF REFERENCE NUMERALS

1 . . . Reactor
2 . . . Flash evaporator
3 . . . First distillation column (splitter column)
4 . . . Decanter
5 . . . Second distillation column
34a, 34b, 35a, 35b . . . Supply line

The invention claimed is:

1. A process for producing acetic acid, comprising:
distilling a mixture containing hydrogen iodide, water, methyl iodide, acetic acid, and methyl acetate to form an overhead containing a lower boiling point component, and condensing the overhead to form separated liquid phases, wherein the mixture contains an effective amount of water in a concentration of not more than 5% by weight and methyl acetate in a concentration of 0.5 to 9% by weight, and is separated, in the distillation step, into the overhead containing methyl iodide and a side cut stream or bottom stream containing acetic acid.

2. The process according to claim 1, wherein the mixture has a methyl acetate concentration of 0.07 to 1.2 mol/L and a water concentration of 0.28 to 2.8 mol/L, and is distilled continuously.

3. The process according to claim 1, wherein the mixture contains 0.5 to 4.5% by weight of water and 0.5 to 8% by weight of methyl acetate, and is subjected to the distillation step.

4. The process according to claim 1, wherein the mixture further contains dimethyl ether.

5. The process according to claim 1, wherein the mixture is fed to a distillation column from an intermediate or lower position of the distillation column in height.

6. The process according to claim 1, wherein a zone having a high water concentration is formed inside a distillation column at a position upper than a position at which the mixture is fed to the distillation column,
in the zone having the high water concentration, hydrogen iodide is allowed to react with methyl acetate for producing methyl iodide and acetic acid, and
the distillation provides the overhead containing the resulting methyl iodide.

7. The process for producing acetic acid according to claim 1, wherein
methanol is allowed to continuously react with carbon monoxide by using a catalyst containing a group 8 metal of the Periodic Table, an ionic iodide, and methyl iodide in the presence of water,
the reaction product is separated into a low-volatile phase component and a volatile phase component by a flash distillation,
the volatile phase component as the mixture is distilled to form the overhead containing methyl iodide and the side cut stream or bottom stream containing acetic acid, and the overhead is condensed to form an aqueous phase and an organic phase,
and wherein the volatile phase component is distilled while being adjusted to a water concentration of an effective amount and not more than 5% by weight and a methyl acetate concentration of 0.5 to 9% by weight in a distillation atmosphere of the volatile phase component in terms of a condensate or liquid form.

8. The process according to claim 1, wherein at least one member selected from the group consisting of methyl acetate, methanol and dimethyl ether, and if necessary water, is added to the volatile phase component as the mixture or a distillation atmosphere thereof as the mixture to adjust the concentrations of water and methyl acetate, and the resulting volatile phase component is distilled.

9. The process according to claim 1, wherein a distillation atmosphere of a volatile phase component is formed in the distillation column at a height equal to or upper than a feed site of the volatile phase component.

10. The process according to claim 1, wherein the mixture contains 1 to 4.3% by weight of water and 0.8 to 7.5% by weight of methyl acetate, and is subjected to the distillation step.

11. The process according to claim 1, wherein the mixture has a hydrogen iodide concentration of 100 to 10000 ppm, and is subjected to a distillation to form the side cut stream having a hydrogen iodide concentration of 1 to 350 ppm.

12. The process according to claim 1, wherein the separated liquid phases are a lower phase and an upper phase, the lower phase has a methyl acetate concentration of 1 to 15% by weight, and the upper phase has a methyl acetate concentration of 0.4 to 8% by weight.

13. A method for improving a liquid-liquid separation of a condensate while reducing a concentration of hydrogen iodide in an overhead and a side cut stream, comprising:

distilling a mixture containing hydrogen iodide, water, methyl iodide, acetic acid, and methyl acetate to form an overhead containing a lower boiling point component, and condensing the overhead to give a condensate containing separated liquid phases, wherein the mixture contains an effective amount of water in a concentration of not more than 5% by weight and methyl acetate in a concentration of 0.5 to 9% by weight.

14. The method according to claim 13, wherein the concentration of hydrogen iodide in the overhead and the side cut stream is reduced by adjusting a concentration of methyl acetate in the mixture to 0.5 to 8% by weight.

15. The method according to claim 13, wherein said method improves the liquid-liquid separation of the condensate, wherein concentrations of methyl iodide and methyl acetate in the lower phase are adjusted to 76 to 98% by weight and 1 to 15% by weight, respectively (with the proviso that the total of components in the lower phase is 100% by weight), and concentrations of water and methyl acetate in the upper phase are adjusted to 50 to 90% by weight and 0.4 to 8% by weight, respectively (with the proviso that the total of components in the upper phase is 100% by weight).

* * * * *

(12) INTER PARTES REVIEW CERTIFICATE (1838th)
United States Patent (10) Number: US 9,006,483 K1
Miura et al. (45) Certificate Issued: Sep. 22, 2020

(54) PROCESS FOR PRODUCING ACETIC ACID

(71) Applicants: Hiroyuki Miura; Hidehiko Nakajima; Masahiko Shimizu; Takashi Ueno

(72) Inventors: Hiroyuki Miura; Hidehiko Nakajima; Masahiko Shimizu; Takashi Ueno

(73) Assignee: DAICEL CORPORATION

Trial Number:
IPR2017-00166 filed Oct. 31, 2016

Inter Partes Review Certificate for:
Patent No.: 9,006,483
Issued: Apr. 14, 2015
Appl. No.: 14/378,049
Filed: Aug. 11, 2014

The results of IPR2017-00166 are reflected in this inter partes review certificate under 35 U.S.C. 318(b).

INTER PARTES REVIEW CERTIFICATE
U.S. Patent 9,006,483 K1
Trial No. IPR2017-00166
Certificate Issued Sep. 22, 2020

AS A RESULT OF THE INTER PARTES REVIEW PROCEEDING, IT HAS BEEN DETERMINED THAT:

Claims 1-3, 5, 6, 9-13 and 15 are cancelled.

\* \* \* \* \*